United States Patent
Liddicoat et al.

(10) Patent No.: US 11,350,944 B2
(45) Date of Patent: *Jun. 7, 2022

(54) APPARATUS AND METHOD FOR THE LIGATION OF TISSUE

(71) Applicant: SentreHEART, Inc., Redwood City, CA (US)

(72) Inventors: John R. Liddicoat, Boston, MA (US); William E. Cohn, Bellaire, TX (US); Roger Laham, Brookline, MA (US)

(73) Assignee: SENTREHEART LLC, Redwood City, CA (US)

( * ) Notice: Subject to any disclaimer, the term of this patent is extended or adjusted under 35 U.S.C. 154(b) by 296 days.

This patent is subject to a terminal disclaimer.

(21) Appl. No.: 16/439,578

(22) Filed: Jun. 12, 2019

(65) Prior Publication Data

US 2019/0290285 A1 Sep. 26, 2019

Related U.S. Application Data

(63) Continuation of application No. 15/041,777, filed on Feb. 11, 2016, now Pat. No. 10,327,780, which is a (Continued)

(51) Int. Cl.
*A61B 17/12* (2006.01)
*A61B 17/00* (2006.01)
(Continued)

(52) U.S. Cl.
CPC .. *A61B 17/12013* (2013.01); *A61B 17/00234* (2013.01); *A61B 17/0467* (2013.01);
(Continued)

(58) Field of Classification Search
CPC .......... A61B 17/00234; A61B 17/0467; A61B 17/12009; A61B 17/12013; A61B 17/30;
(Continued)

(56) References Cited

U.S. PATENT DOCUMENTS 3,435,905 A 4/1969 Lazarus
3,496,932 A 2/1970 Prisk et al.
(Continued)

FOREIGN PATENT DOCUMENTS

CN 101242785 A 8/2008
CN 1822794 B 5/2010
(Continued)

OTHER PUBLICATIONS afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.
(Continued)

*Primary Examiner* — Jocelin C Tanner
(74) *Attorney, Agent, or Firm* — Levine Bagade Han LLP

(57) ABSTRACT

A novel catheter-based system which ligates the left atrial appendage (LAA) on the outside of the heart, preferably using a combination of catheters and/or instruments, e.g., a guide catheter positioned inside the left atrial appendage which may assist in locating the left atrial appendage and/or assist in the optimal placement of a ligature on the outside of the appendage, and a ligating catheter and/or instrument outside the heart in the pericardial space to set a ligating element at the neck of the left atrial appendage.

15 Claims, 32 Drawing Sheets

Related U.S. Application Data continuation of application No. 12/124,023, filed on May 20, 2008, now Pat. No. 9,271,819, which is a continuation of application No. 10/963,371, filed on Oct. 11, 2004, now Pat. No. 7,846,168.

(60) Provisional application No. 60/528,995, filed on Dec. 12, 2003, provisional application No. 60/510,100, filed on Oct. 9, 2003.

(51) Int. Cl.
| | |
|---|---|
| *A61B 17/04* | (2006.01) |
| *A61B 17/30* | (2006.01) |
| *A61M 25/01* | (2006.01) |
| *A61M 25/10* | (2013.01) |
| *A61M 29/02* | (2006.01) |
| *A61B 90/00* | (2016.01) |

(52) U.S. Cl.
CPC ........ *A61B 17/12009* (2013.01); *A61B 17/30* (2013.01); *A61M 25/0108* (2013.01); *A61M 25/0127* (2013.01); *A61M 25/10* (2013.01); *A61M 29/02* (2013.01); *A61B 2017/00243* (2013.01); *A61B 2017/00867* (2013.01); *A61B 2017/00876* (2013.01); *A61B 2017/12018* (2013.01); *A61B 2017/308* (2013.01); *A61B 2090/0811* (2016.02); *A61B 2090/3966* (2016.02); *A61B 2576/023* (2013.01); *A61F 2230/005* (2013.01); *A61F 2230/0006* (2013.01)

(58) Field of Classification Search
CPC ...... A61B 2017/1218; A61B 2017/308; A61B 2090/3966; A61B 2090/0811; A61B 2576/023; A61M 25/0108; A61M 25/0127; A61M 25/10; A61M 29/02; A61F 2230/0006; A61F 2230/005
See application file for complete search history.

(56) References Cited

U.S. PATENT DOCUMENTS

| | | | |
|---|---|---|---|
| 3,677,597 A | 7/1972 | Stipek | |
| 3,802,074 A | 4/1974 | Hoppe | |
| 3,805,791 A | 4/1974 | Seuberth et al. | |
| 3,828,790 A | 8/1974 | Curtiss et al. | |
| 3,841,685 A | 10/1974 | Kolodziej | |
| 3,999,555 A | 12/1976 | Person | |
| 4,018,229 A | 4/1977 | Komiya | |
| 4,030,509 A | 6/1977 | Heilman et al. | |
| 4,078,305 A | 3/1978 | Akiyama | |
| 4,181,123 A | 1/1980 | Crosby | |
| 4,249,536 A | 2/1981 | Vega | |
| 4,257,278 A | 3/1981 | Papadofrangakis et al. | |
| 4,319,562 A | 3/1982 | Crosby | |
| 4,428,375 A | 1/1984 | Ellman | |
| 4,596,530 A | 6/1986 | McGlinn | |
| 4,662,377 A | 5/1987 | Heilman et al. | |
| 4,765,341 A | 8/1988 | Mower et al. | |
| 4,817,608 A | 4/1989 | Shapland et al. | |
| 4,901,405 A | 2/1990 | Grover et al. | |
| 4,944,753 A | 7/1990 | Burgess et al. | |
| 4,991,578 A | 2/1991 | Cohen | |
| 4,991,603 A | 2/1991 | Cohen et al. | |
| 4,998,975 A | 3/1991 | Cohen et al. | |
| 5,033,477 A | 7/1991 | Chin et al. | |
| 5,108,406 A | 4/1992 | Lee | |
| 5,163,942 A | 11/1992 | Rydell | |
| 5,163,946 A | 11/1992 | Li | |
| 5,176,691 A | 1/1993 | Pierce | |
| 5,181,123 A | 1/1993 | Swank | |
| 5,181,919 A | 1/1993 | Bergman et al. | |
| 5,226,535 A | 7/1993 | Roshdy et al. | |
| 5,226,908 A | 7/1993 | Yoon | |
| 5,242,459 A | 9/1993 | Buelna | |
| 5,243,977 A | 9/1993 | Trabucco et al. | |
| 5,269,326 A | 12/1993 | Verrier | |
| 5,279,539 A | 1/1994 | Bohan et al. | |
| 5,281,238 A | 1/1994 | Chin et al. | |
| 5,300,078 A | 4/1994 | Buelna | |
| 5,306,234 A | 4/1994 | Johnson | |
| 5,312,423 A | 5/1994 | Rosenbluth et al. | |
| 5,318,578 A | 6/1994 | Hasson | |
| 5,336,229 A | 8/1994 | Noda | |
| 5,336,231 A | 8/1994 | Adair | |
| 5,336,252 A | 8/1994 | Cohen | |
| 5,385,156 A | 1/1995 | Oliva | |
| 5,387,219 A | 2/1995 | Rappe | |
| 5,398,944 A | 3/1995 | Holster | |
| 5,403,331 A | 4/1995 | Chesterfield et al. | |
| 5,405,351 A | 4/1995 | Kinet et al. | |
| 5,417,684 A | 5/1995 | Jackson et al. | |
| 5,423,821 A | 6/1995 | Pasque | |
| 5,423,830 A | 6/1995 | Schneebaum et al. | |
| 5,433,457 A | 7/1995 | Wright | |
| 5,433,730 A | 7/1995 | Alt | |
| 5,443,481 A | 8/1995 | Lee | |
| 5,449,361 A | 9/1995 | Preissman | |
| 5,449,637 A | 9/1995 | Kadry | |
| 5,465,731 A | 11/1995 | Bell et al. | |
| 5,494,240 A | 2/1996 | Waugh | |
| 5,498,228 A | 3/1996 | Royalty et al. | |
| 5,522,819 A | 6/1996 | Graves et al. | |
| 5,540,711 A | 7/1996 | Kieturakis et al. | |
| 5,545,178 A | 8/1996 | Kensey et al. | |
| 5,571,161 A * | 11/1996 | Starksen | A61M 25/1002 604/161 |
| 5,591,177 A | 1/1997 | Lehrer | |
| 5,609,597 A | 3/1997 | Lehrer | |
| 5,624,430 A | 4/1997 | Eton et al. | |
| 5,624,453 A | 4/1997 | Ahmed | |
| 5,634,895 A | 6/1997 | Igo et al. | |
| 5,636,780 A | 6/1997 | Green et al. | |
| 5,676,162 A | 10/1997 | Larson, Jr. et al. | |
| 5,676,651 A | 10/1997 | Larson, Jr. et al. | |
| 5,678,547 A | 10/1997 | Faupel et al. | |
| 5,681,278 A | 10/1997 | Igo et al. | |
| 5,682,906 A | 11/1997 | Sterman et al. | |
| 5,683,348 A | 11/1997 | Diener | |
| 5,683,364 A | 11/1997 | Zadini et al. | |
| 5,683,445 A | 11/1997 | Swoyer | |
| 5,693,059 A | 12/1997 | Yoon | |
| 5,693,091 A | 12/1997 | Larson, Jr. et al. | |
| 5,699,748 A | 12/1997 | Linskey, Jr. et al. | |
| 5,702,430 A | 12/1997 | Larson, Jr. et al. | |
| 5,707,336 A | 1/1998 | Rubin | |
| 5,716,367 A | 2/1998 | Koike et al. | |
| 5,716,392 A | 2/1998 | Bourgeois et al. | |
| 5,727,569 A | 3/1998 | Benetti et al. | |
| 5,728,151 A | 3/1998 | Garrison et al. | |
| 5,735,877 A | 4/1998 | Pagedas | |
| 5,741,281 A | 4/1998 | Martin | |
| 5,752,526 A | 5/1998 | Cosgrove | |
| 5,766,151 A | 6/1998 | Valley et al. | |
| 5,766,216 A | 6/1998 | Gangal et al. | |
| 5,766,217 A | 6/1998 | Christy | |
| 5,769,863 A | 6/1998 | Garrison | |
| 5,779,727 A | 7/1998 | Orejola | |
| 5,788,715 A | 8/1998 | Watson, Jr. et al. | |
| 5,792,151 A | 8/1998 | Heck et al. | |
| 5,797,870 A | 8/1998 | March et al. | |
| 5,797,929 A | 8/1998 | Andreas et al. | |
| 5,797,946 A | 8/1998 | Chin | |
| 5,799,661 A | 9/1998 | Boyd et al. | |
| 5,810,845 A | 9/1998 | Yoon | |
| 5,814,052 A | 9/1998 | Nakao et al. | |
| 5,823,946 A | 10/1998 | Chin | |
| 5,827,216 A | 10/1998 | Igo et al. | |
| 5,840,059 A | 11/1998 | March et al. | |
| 5,851,185 A * | 12/1998 | Berns | A61B 17/11 600/434 |

(56) References Cited

U.S. PATENT DOCUMENTS

| | | | |
|---|---|---|---|
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,895,404 A | 4/1999 | Ruiz |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,957,936 A | 9/1999 | Yoon et al. |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,045,570 A | 4/2000 | Epstein et al. |
| 6,048,329 A | 4/2000 | Thompson et al. |
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,132,439 A | 10/2000 | Kontos |
| 6,148,230 A | 11/2000 | KenKnight |
| 6,149,595 A | 11/2000 | Seitz et al. |
| 6,152,144 A * | 11/2000 | Lesh ................. A61B 17/0057 128/898 |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,985,776 B2 * | 1/2006 | Kane ..................... A61N 1/056 600/585 |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,597,705 B2 | 10/2009 | Forsberg et al. |
| 7,608,091 B2 | 10/2009 | Goldfarb et al. |
| 7,610,104 B2 | 10/2009 | Kaplan et al. |
| 7,618,425 B2 | 11/2009 | Yamamoto et al. |
| 7,722,641 B2 | 5/2010 | van der Burg et al. |
| 7,758,594 B2 | 7/2010 | Lamson et al. |
| 7,828,810 B2 * | 11/2010 | Liddicoat ......... A61B 17/12009 606/139 |
| 7,842,051 B2 | 11/2010 | Dana et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 7,967,808 B2 | 6/2011 | Fitzgerald et al. |
| 8,070,693 B2 | 12/2011 | Ayala et al. |
| 8,075,573 B2 | 12/2011 | Gambale et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,636,767 B2 | 1/2014 | McClain |
| 8,647,367 B2 | 2/2014 | Kassab et al. |
| 8,715,302 B2 | 5/2014 | Ibrahim et al. |
| 8,771,297 B2 | 7/2014 | Miller et al. |
| 8,795,297 B2 | 8/2014 | Liddicoat et al. |
| 8,795,310 B2 | 8/2014 | Fung et al. |
| 8,814,778 B2 | 8/2014 | Kiser et al. |
| 8,932,276 B1 | 1/2015 | Morriss et al. |
| 8,961,543 B2 | 2/2015 | Friedman et al. |
| 8,986,325 B2 | 3/2015 | Miller et al. |
| 9,089,324 B2 | 7/2015 | McCaw et al. |
| 9,144,428 B2 | 9/2015 | Binmoeller et al. |
| 9,186,174 B2 | 11/2015 | Krishnan et al. |

(56) References Cited

U.S. PATENT DOCUMENTS

| | | |
|---|---|---|
| 9,198,664 B2 | 12/2015 | Fung et al. |
| 9,198,683 B2 | 12/2015 | Friedman et al. |
| 9,271,819 B2 | 3/2016 | Liddicoat et al. |
| 9,339,295 B2 | 5/2016 | Fung et al. |
| 9,408,608 B2 | 8/2016 | Clark et al. |
| 9,456,818 B2 | 10/2016 | Torrie |
| 9,498,206 B2 | 11/2016 | Fung et al. |
| 9,498,223 B2 | 11/2016 | Miller et al. |
| 9,522,006 B2 | 12/2016 | Liddicoat et al. |
| 10,045,784 B2 | 8/2018 | Friedman et al. |
| 10,327,780 B2 * | 6/2019 | Liddicoat ............ A61M 25/0108 |
| 10,716,571 B2 | 7/2020 | Fung et al. |
| 10,799,241 B2 | 10/2020 | Fung et al. |
| 10,806,460 B2 | 10/2020 | Liddicoat et al. |
| 10,959,734 B2 | 3/2021 | Fung et al. |
| 10,966,725 B2 | 4/2021 | Miller et al. |
| 11,020,122 B2 | 6/2021 | Miller et al. |
| 11,026,690 B2 | 6/2021 | Fung et al. |
| 11,207,073 B2 | 12/2021 | Clark et al. |
| 2001/0007070 A1 | 7/2001 | Stewart et al. |
| 2001/0025132 A1 | 9/2001 | Alferness et al. |
| 2002/0016564 A1 | 2/2002 | Courtney et al. |
| 2002/0017306 A1 | 2/2002 | Cox et al. |
| 2002/0022860 A1 | 2/2002 | Borillo et al. |
| 2002/0049457 A1 * | 4/2002 | Kaplan ................ A61B 17/122 606/139 |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2002/0147456 A1 | 10/2002 | Diduch et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0065271 A1 | 4/2003 | Koury |
| 2003/0069577 A1 | 4/2003 | Vaska et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0236535 A1 | 12/2003 | Onuki et al. |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059352 A1 | 3/2004 | Burbank et al. |
| 2004/0064138 A1 | 4/2004 | Grabek |
| 2004/0068267 A1 | 4/2004 | Harvie et al. |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 * | 6/2004 | Chin .................... A61N 1/0587 606/151 |
| 2004/0116943 A1 | 6/2004 | Brandt et al. |
| 2004/0148020 A1 | 7/2004 | Vidlund et al. |
| 2004/0158127 A1 | 8/2004 | Okada |
| 2004/0162579 A1 | 8/2004 | Foerster |
| 2004/0199236 A1 | 10/2004 | Laske et al. |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 * | 12/2004 | Wan ...................... A61B 34/70 606/1 |
| 2005/0033274 A1 | 2/2005 | Pless et al. |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043743 A1 | 2/2005 | Dennis |
| 2005/0043745 A1 | 2/2005 | Alferness et al. |
| 2005/0080454 A1 | 4/2005 | Drews et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0165466 A1 | 7/2005 | Morris et al. |
| 2005/0182417 A1 | 8/2005 | Pagano |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0095066 A1 | 5/2006 | Chang et al. |
| 2006/0100545 A1 | 5/2006 | Ayala et al. |
| 2006/0106278 A1 | 5/2006 | Machold et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2007/0010829 A1 | 1/2007 | Nobles et al. |
| 2007/0016228 A1 | 1/2007 | Salas |
| 2007/0027456 A1 | 2/2007 | Gartner et al. |
| 2007/0038229 A1 | 2/2007 | de la Torre |
| 2007/0060951 A1 | 3/2007 | Shannon |
| 2007/0083082 A1 | 4/2007 | Kiser et al. |
| 2007/0083225 A1 | 4/2007 | Kiser et al. |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin |
| 2008/0009843 A1 | 1/2008 | de la Torre |
| 2008/0015406 A1 | 1/2008 | Dlugos et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0065156 A1 | 3/2008 | Hauser et al. |
| 2008/0097489 A1 | 4/2008 | Goldfarb et al. |
| 2008/0154260 A1 | 6/2008 | Hoof |
| 2008/0177179 A1 | 7/2008 | Stubbs et al. |
| 2008/0228265 A1 | 9/2008 | Spence et al. |
| 2008/0245371 A1 | 10/2008 | Gruber |
| 2008/0269782 A1 | 10/2008 | Stefanchik et al. |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0088728 A1 | 4/2009 | Dollar et al. |
| 2009/0088778 A1 | 4/2009 | Miyamoto et al. |
| 2009/0124847 A1 | 5/2009 | Doty et al. |
| 2009/0131749 A1 | 5/2009 | Ahmed et al. |
| 2009/0182326 A1 | 7/2009 | Zenati et al. |
| 2009/0196696 A1 | 8/2009 | Otsuka et al. |
| 2010/0069925 A1 | 3/2010 | Friedman et al. |
| 2010/0094314 A1 | 4/2010 | Hernlund |
| 2010/0174296 A1 | 7/2010 | Vakharia et al. |
| 2010/0191253 A1 | 7/2010 | Oostman et al. |
| 2010/0204716 A1 | 8/2010 | Stewart et al. |
| 2010/0331820 A1 | 12/2010 | Giuseppe et al. |
| 2011/0034804 A1 | 2/2011 | Hubregtse et al. |
| 2011/0060350 A1 | 3/2011 | Powers et al. |
| 2011/0087270 A1 | 4/2011 | Penner et al. |
| 2011/0092997 A1 | 4/2011 | Kang |
| 2011/0106107 A1 | 5/2011 | Binmoeller et al. |
| 2011/0112537 A1 | 5/2011 | Bernstein et al. |
| 2011/0112569 A1 | 5/2011 | Friedman et al. |
| 2011/0144660 A1 | 6/2011 | Liddicoat et al. |
| 2011/0295060 A1 | 12/2011 | Zenati et al. |
| 2012/0022558 A1 | 1/2012 | Friedman et al. |
| 2012/0209300 A1 | 8/2012 | Torrie |

(56) References Cited

U.S. PATENT DOCUMENTS

| | | |
|---|---|---|
| 2012/0323262 A1 | 12/2012 | Ibrahim et al. |
| 2012/0330351 A1 | 12/2012 | Friedman et al. |
| 2014/0018831 A1 | 1/2014 | Kassab et al. |
| 2014/0171733 A1 | 6/2014 | Sternik |
| 2014/0222138 A1 | 8/2014 | Machold et al. |
| 2014/0276911 A1 | 9/2014 | Smith et al. |
| 2014/0330074 A1 | 11/2014 | Morriss et al. |
| 2014/0336572 A1 | 11/2014 | Heisel et al. |
| 2014/0336676 A1 | 11/2014 | Pong et al. |
| 2014/0364901 A1 | 12/2014 | Kiser et al. |
| 2014/0364907 A1 | 12/2014 | White et al. |
| 2015/0018853 A1 | 1/2015 | Friedman et al. |
| 2015/0025312 A1 | 1/2015 | de Canniere |
| 2015/0173765 A1 | 1/2015 | Friedman et al. |
| 2015/0119884 A1 | 4/2015 | Fung et al. |
| 2015/0157328 A1 | 6/2015 | Miller et al. |
| 2015/0182225 A1 | 7/2015 | Morejohn et al. |
| 2015/0190135 A1 | 7/2015 | Ibrahim et al. |
| 2015/0223813 A1 | 8/2015 | Willisamson et al. |
| 2015/0250482 A1 | 9/2015 | Slaughter et al. |
| 2015/0272618 A1 | 10/2015 | Fung et al. |
| 2015/0313633 A1 | 11/2015 | Gross et al. |
| 2015/0374380 A1 | 12/2015 | Miller et al. |
| 2016/0008001 A1 | 1/2016 | Winkler et al. |
| 2016/0106421 A1 | 4/2016 | Eliachar et al. |
| 2016/0120549 A1 | 5/2016 | Fung et al. |
| 2016/0235412 A1 | 8/2016 | Liddicoat et al. |
| 2016/0249932 A1 | 9/2016 | Rogers et al. |
| 2016/0310144 A1 | 10/2016 | Kimura et al. |
| 2016/0317155 A1 | 11/2016 | Kimura et al. |
| 2016/0346028 A1 | 12/2016 | Rogers et al. |
| 2017/0290591 A1 | 10/2017 | Liddicoat et al. |
| 2017/0290592 A1 | 10/2017 | Miller et al. |
| 2018/0008342 A1 | 1/2018 | Ibrahim et al. |
| 2018/0085130 A1 | 3/2018 | Fung et al. |
| 2018/0325523 A1 | 11/2018 | Friedman et al. |
| 2021/0015483 A1 | 1/2021 | Fung et al. |

FOREIGN PATENT DOCUMENTS

| | | |
|---|---|---|
| CN | 101262823 B | 12/2011 |
| CN | 105263425 B | 7/2018 |
| EP | 0 598 219 B1 | 5/1994 |
| EP | 0 625 336 A2 | 11/1994 |
| EP | 0 629 381 A2 | 12/1994 |
| EP | 0 705 566 A1 | 4/1996 |
| EP | 1 010 397 A | 6/2000 |
| GB | 1 506 142 A | 4/1978 |
| JP | H-6-319742 A | 11/1994 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-512071 A | 4/2002 |
| JP | 2002-540834 A | 12/2002 |
| JP | 2002-540901 A | 12/2002 |
| JP | 2003-225241 A | 8/2003 |
| JP | 2004-000601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| JP | 2010-523171 A | 7/2010 |
| JP | 2012-522596 A | 9/2012 |
| RU | 2088162 C1 | 8/1997 |
| WO | WO-94/01045 A1 | 1/1994 |
| WO | WO-94/04079 A1 | 3/1994 |
| WO | WO-94/08514 A1 | 4/1994 |
| WO | WO-96/04854 A1 | 2/1996 |
| WO | WO-96/40356 A1 | 12/1996 |
| WO | WO-97/11644 A1 | 4/1997 |
| WO | WO-97/43957 A1 | 11/1997 |
| WO | WO-99/53845 A1 | 10/1999 |
| WO | WO-00/59383 A1 | 10/2000 |
| WO | WO-00/61202 A1 | 10/2000 |
| WO | WO-2003/022133 A2 | 3/2003 |
| WO | WO-2003/022133 A3 | 3/2003 |
| WO | WO-2003/059174 A2 | 7/2003 |
| WO | WO-2003/059174 A3 | 7/2003 |
| WO | WO-2003/070133 A1 | 8/2003 |
| WO | WO-2004/002327 A1 | 1/2004 |
| WO | WO-2004/066828 A2 | 8/2004 |
| WO | WO-2004/066828 A3 | 8/2004 |
| WO | WO-2004103189 A1 | 12/2004 |
| WO | WO-2005/034767 A1 | 4/2005 |
| WO | WO-2005/034802 A2 | 4/2005 |
| WO | WO-2005/034802 A3 | 4/2005 |
| WO | WO-2005/084127 A2 | 9/2005 |
| WO | WO-2005/084127 A3 | 9/2005 |
| WO | WO-2006/096805 A1 | 9/2006 |
| WO | WO-2006/110734 A2 | 10/2006 |
| WO | WO-2006/115689 A1 | 11/2006 |
| WO | WO-2007/001936 A2 | 1/2007 |
| WO | WO-2007/001936 A3 | 1/2007 |
| WO | WO-2007/037516 A2 | 4/2007 |
| WO | WO-2007/037516 A3 | 4/2007 |
| WO | WO-2007/056502 A1 | 5/2007 |
| WO | WO-2008/017080 A2 | 2/2008 |
| WO | WO-2008/017080 A3 | 2/2008 |
| WO | WO-2008/036408 A2 | 3/2008 |
| WO | WO-2008/036408 A3 | 3/2008 |
| WO | WO-2008/121278 A2 | 10/2008 |
| WO | WO-2009/039191 A2 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/115030 A1 | 10/2010 |
| WO | WO-2012/170652 A1 | 12/2012 |
| WO | WO-2014/164028 A1 | 10/2014 |
| WO | WO-2016/005902 A1 | 1/2016 |

OTHER PUBLICATIONS

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Age-ing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

Benjamin, B.A. et al. (1994). "Effect of Bilateral Atrial Appendectomy on Postprandial Sodium Excretion in Conscious Monkeys," *Society for Experimental Biology and Medicine* 2006: 1 page.

Beygui, F. et al. (2005, e-pub. Oct. 21, 2005). "Multimodality Imaging of Percutaneous Closure of the Left Atrial Appendage," *Clinical Vignette*, 1 page.

Bisleri, G. et al. (Jun. 3, 2005). "Innovative Monolateral Approach for Closed-Chest Atrial Fibrillation Surgery," *The Annals of Thoracic Surgery* 80:e22-e25.

Björk, V.O. et al. (Aug. 1961). "Sequelae of Left Ventricular Puncture with Angiocardiography," *Circulation* 24:204-212.

Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.

Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.

(56) References Cited

OTHER PUBLICATIONS

Bonanomi, G. et al. (Jan. 1, 2003). "Left Atrial Appendectomy and Maze," *Journal of the American College of Cardiology* 41(1):169-171.
Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.
Botham, R.J. et al. (May 1959). "Pericardial Tamponade Following Percutaneous Left Ventricular Puncture," *Circulation* 19:741-744.
Brock, R. et al. (1956). "Percutaneous Left Ventricular Puncture in the Assessment of Aortic Stenosis," *Thorax* 11:163-171.
Burke, R.P. et al. (1992). "Improved Surgical Approach to Left Atrial Appendage Aneurysm," *Journal of Cardiac Surgery* 7(2):104-107.
Canaccord Adams (Aug. 11, 2008). "A-Fib: Near A Tipping Point," 167 pages.
Chung, M.K. (Jul. 2003). "Current Clinical Issues in Atrial Fibrillation," *Cleveland Clinic Journal of Medicine* 70(Supp. 3):S6-S11.
Coffin, L.H. (Jun. 1985). "Use of the Surgical Stapler to Obliterate the Left Atrial Appendage," *Surgery, Gynecology & Obstetric* 160:565-566.
Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.
Costa, R. et al. (2006). "Bi-Atrial Subxiphoid Epicardial Pacemaker in Superior Vena Cava Syndrome," *Arq. Bras. Cardiol.* 87:e45-e47.
Cox, J.L. et al. (Apr. 1991). "The Surgical Treatment of Atrial Fibrillation: IV. Surgical Technique," *J. Thorac. Cardiovasc. Surg.* 101(4):584-592.
Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.
Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.
Cox, J.L. et al. (Nov. 1999). "Impact of the Maze Procedure on the Stroke Rate in Patients with Atrial Fibrillation," *J. Thorac. Cardiovasc. Surg.* 118:833-840.
Cox, J.L. et al. (2004). "The Role of Surgical Intervention in the Management of Atrial Fibrillation," *Texas Heart Institute Journal* 31(3):257-265.
Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.
D'Avila, A. et al. (Apr. 2003). "Pericardial Anatomy for the Interventional Electrophysiologist," *Journal of Cardiovascular Electrophysiology* 14(4):422-430.
D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.
Demaria, A.N. et al. (Dec. 17, 2003). "Highlights of the Year JACC 2003," *Journal of the American College of Cardiology* 42(12):2156-2166.
Deneu, S. et al. (Jul. 11, 1999). "Catheter Entrapment by Atrial Suture During Minimally Invasive Port-access Cardiac Surgery," *Canadian Journal of Anesthesia* 46(10):983-986.
Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.
Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.
Donnino, R. et al. (2007). "Left Atrial Appendage Thrombus Outside of a 'Successful' Ligation," *European Journal of Echocardiography* pp. 1-2.
Dullum, M.K.C. et al. (1999). "Xyphoid MIDCAB: Report of the Technique and Experience with a Less Invasive MIDCAB Procedure," *Heart Surgery Forum* 2(1):77-81.
Feinberg, W.M. et al. (Mar. 13, 1995). "Prevalence, Age Distribution, and Gender of Patients With Atrial Fibrillation," *Arch Intern Med* 155:469-473.
Fieguth, H.G. et al. (1997). "Inhibition of Atrial Fibrillation by Pulmonary Vein Isolation and Auricular Resection—Experimental Study in A Sheep Model," *European Journal of Cardio-Thoracic Surgery* 11:714-721.
Fisher, D.C. et al. (Dec. 1998). "Large Gradient Across a Partially Ligated Left Atrial Appendage," *Journal of the American Society of Echocardiography* 11(12):1163-1165.
Friberg, L. et al. (2006). "Stroke Prophylaxis in Atrial Fibrillation: Who Gets it and Who Does Not?" *European Heart Journal* 27:1954-1964.
Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.
Fuster, V. et al. (Oct. 2001). "ACC/AHA/ESC Guidelines for the Management of Patients with Atrial Fibrillation," *European Heart Journal* 22(20):1852-1923.
Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.
Gardiner, G.A. Jr. et al. (Apr. 1986). "Complications of Transluminal Angioplasty," *Radiology* 159:201-208.
Gillinov, A.M. (2007). "Advances in Surgical Treatment of Atrial Fibrillation," *Stroke* 38(part 2):618-623.
Gilman, R.A. et al. (Apr. 1963). "Direct Left Ventricular Puncture," *California Medicine* 98(4):200-203.
Goodwin, W.E. et al. (Nov. 1950). "Translumbar Aortic Puncture and Retrograde Catheterization of the Aorta In Aortography and Renal Arteriography," *Annals of Surgery* 132(5):944-958.
Gottlieb, L.K. et al. (Sep. 12, 1994). "Anticoagulation in Atrial Fibrillation," *Arch Intern Med.* 154:1945-1953.
Graffigna, A. et al. (1993). "Surgical Treatment of Wolff-Parkinson-White Syndrome: Epicardial Approach Without the Use of Cardiopulmonary Bypass," *J. Card. Surg.* 8:108-116.
Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.
Halperin, J.L. et al. (Aug. 1988). "Atrial Fibrillation and Stroke: New Ideas, Persisting Dilemmas," *Journal of the American Heart Association* 19(8):937-941.
Halperin, J.L. et al. (Oct. 1, 2003). "Obliteration of the Left Atrial Appendage for Prevention of Thromboembolism," *Journal of the American College of Cardiology* 42(7):1259-1261.
Hammill, S.C. (May 2006). "Epicardial Ablation: Reducing the Risks," *J. Cardiovasc. Electrophysiol.* 17:550-552.
Hara, H. et al. (Jan. 2008). "Percutaneous Left Atrial Appendage Obliteration," *JACC: Cardiovascular Imagin* 1(1):92-93.
Hart, R.G. et al. (Nov. 2, 1999). "Atrial Fibrillation and Thromboembolism: A Decade of Progress in Stroke Prevention," *Annals of Internal Medicine* 131(9):688-695.
Hart, R.G. et al. (2001). "Atrial Fibrillation and Stroke: Concepts and Controversies," *Stroke* 32:803-808.
Hart, R.G. (Sep. 11, 2003). "Atrial Fibrillation and Stroke Prevention," *The New England Journal of Medicine* 349(11):1015-1016.
Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at the Canadian Cardiovascular Congress 2003, Toronto, Canada, Abstract No. 666, 2 pages.
Healey, J.S. et al. (Aug. 2005). "Left Atrial Appendage Occlusion Study (LAAOS): Results of a Randomized Controlled Pilot Study

(56) References Cited

OTHER PUBLICATIONS of Left Atrial Appendage Occlusion During Coronary Bypass Surgery in Patients At Risk for Stroke," *American Heart Journal* 150(2):288-293.
Hein, R. et al. (2005). "Patent Foramen Ovale and Left Atrial Appendage: New Devices and Methods for Closure," *Pediatric Cardiology* 26(3):234-240.
Heist, E.K. et al. (Nov. 2006). "Analysis of the Left Atrial Appendage by Magnetic Resonance Angiography in Patients with Atrial Fibrillation," *Heart Rhythm* 3(11):1313-1318.
Ho, I. et al. (Apr. 24, 2007). "Percutaneous Epicardial Mapping Ablation of a Posteroseptal Accessory Pathway," *Circulation* 115:e418-e421.
Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.
Hoit, B.D. et al. (Jan. 1993). "Altered Left Atrial Compliance After Atrial Appendectomy. Influence on Left Atrial and Ventricular Filling," *Circulation Research* 72(1):167-175.
Inoue, Y. et al. (Jul.-Aug. 1997). "Video Assisted Thoracoscopic and Cardioscopic Radiofrequency Maze Ablation," *Asaio Journal* 43(4):334-337, Abstract Only.
Jaïs, P. et al. (2003). "Radiofrequency Ablation for Atrial Fibrillation," *European Society of Cardiology* 5(Supplement H):H34-H39.
Johnson, W.D. et al. (2000). "The Left Atrial Appendage: Our Most Lethal Human Attachment! Surgical Implications," *Euro. J. Cardiothoracic. Surg.* 17:718-722.
Jongbloed, M.R.M. et al. (2005). "Clinical Applications of Intracardiac Echocardiography in Interventional Procedures," *Heart* 91:981-990.
Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.
Kanderian, A.S. et al. (2008). "Success of Surgical Left Atrial Appendage Closure: Assessment by Transesophageal Echocardiography," *Journal of the American College of Cardiology* 52(11):924-929.
Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.
Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.
Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.
Kerut, E.K. et al. (Jul. 2008). "Anatomy of the Left Atrial Appendage," *Echocardiography* 25(6):669-673.
Khargi, K. et al. (2005). "Surgical Treatment of Atrial Fibrillation: A Systematic Review," *European Journal of Cardiothoracic Surgery* 27:258-265.
Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.
Kistler, P.M. et al. (May 2007). "The Left Atrial Appendage: Not Just an Innocent Bystander," *J. Cardiovasc Electrophysiol* 18(5):465-466.
Klein, H. et al. (Apr. 1990). "The Implantable Automatic Cardioverter-Defibrillator," *Herz* 15(2):111-125, Abstract Only.
Kolb, C. et al. (Feb. 2004). "Incidence of Antitachycardia Therapy Suspension Due to Magnet Reversion in Implantable Cardioverter Defibrillators," *Pace* 27:221-223.
Krikorian, J.G. et al. (Nov. 1978). "Pericardiocentesis," *Am. J. Med.* 65(5):808-814.
Krum, D. et al. (2004). "Visualization of Remnants of the left Atrial Appendage Following Epicardial Surgical Removal," *Heart Rhythm* 1:249.

Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.
Lacomis, J.M. et al. (2007, e-pub. Oct. 17, 2007). "Dynamic Multidimensional Imaging of the Human Left Atrial Appendage," *Europace* 9:1134-1140.
Lee, R. et al. (1999). "The Closed Heart Maze: A Nonbypass Surgical Technique," *The Annals of Thoracic Surgery* 67:1696-1702.
Levinson, M.L. et al. (1998). "Minimally Invasive Atrial Septal Defect Closure Using the Subxyphoid Approach," *Heart Surg. Forum* 1(1):49-53, Abstract Only.
Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.
Li, H. (2007). "Magnet Decoration, Beautiful But Potentially Dangerous For Patients with Implantable Pacemakers or Defibrillators," *Heart Rhythm* 4(1):5-6.
Lindsay, B.D. (1996). "Obliteration of the Left Atrial Appendage: A Concept Worth Testing," *The Annals of Thoracic Surgery* 61:515.
Lip, G.Y.H. et al. (Jun. 2001). "Thromboprophylaxis for Atrial Flutter," *European Heart Journal* 22(12):984-987.
Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.
Macris, M. et al. (Jan. 1999). "Minimally Invasive Access of the Normal Pericardium: Initial Clinical Experience with a Novel Device," *Clin. Cardiol.* 22(Suppl. I):I-36-I-39.
Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I):I-17-I-22.
Mannam, A.P. et al. (Apr. 1, 2002). "Safety of Subxyphoid Pericardial Access Using a Blunt-Tip Needle," *The American Journal of Cardiology* 89:891-893.
Mattox, K.L. et al. (May 1997). "Newer Diagnostic Measure and Emergency Management," *Ches Surg Clin N Am.* 7(2):213-226, Abstract Only.
Mccarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.
Mccaughan, J.J. Jr., et al. (Nov. 1957). "Aortography Utilizing Percutaneous Left Ventricular Puncture," located at <http://www.archsurg.com>, last visited on Apr. 7, 2009, 73:746-751, Abstract Only.
Mcclelland, R.R. (1978). "Congenital Aneurysmal Dilatation of the Left Auricle Demonstrated by Sequential Cardiac Blood-Pool Scintiscanning," *J. Nucl. Med.* 19(5):507-509.
Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.
Miller, P.S.J. et al. (Feb. 2005). "Are Cost Benefits of Anticoagulation for Stroke Prevention in Atrial Fibrillation Underestimated?" *Stroke* 36:360-366.
Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.
Morris, J.J. Jr. (1979). "Transvenous versus Transthoracic Cardiac Pacing," Chapter 16 in *Cardiac Pacing: A Concise Guide to Clinical Practice*, pp. 239-245.
Mráz, T. et al. (Apr. 2007). "Role of Echocardiography in Percutaneous Occlusion of the left Atrial Appendage," *Echocardiography* 24(4):401-404.
Naclerio, E.A. et al. (1979). "Surgical Techniques for Permanent Ventricular Pacing," Chapter 10 in *Cardiac Pacing: A Concise Guide to Clinical Practice*, pp. 145-168.
Nakai, T. et al. (May 7, 2002). "Percutaneous Left Atrial Appendage Occlusion (PLAATO) for Preventing Cardioembolism: First Experience in Canine Model," *Circulation* 105:2217-2222.

(56) References Cited

OTHER PUBLICATIONS

Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.
Odell, J.A. et al. (1996). "Thorascopic Obliteration of the Left Atrial Appendage: Potential for Stroke Reduction?" *Ann. Thorac. Surg.* 61:565-569.
O'Donnell, M. et al. (2005). "Emerging Therapies for Stroke Prevention in Atrial Fibrillation," *European Heart Journal* 7(Supplement C):C19-C27.
Omran, H. et al. (1997). "Left Atrial Appendage Function in Patients with Atrial Flutter," *Heart* 78:250-254.
Onalan, O. et al. (2005). "Nonpharmacologic Stroke Prevention in Atrial Fibrillation," *Expert Rev. Cardiovasc. Ther.* 3(4):619-633.
Onalan, O. et al. (2007). "Left Atrial Appendage Exclusion for Stroke Prevention in Patients With Nonrheumatic Atrial Fibrillation," *Stroke* 38(part2):624-630.
Ostermayer, S. et al. (2003). "Percutaneous Closure of the Left Atrial Appendage," *Journal of Interventional Cardiology* 16(6):553-556.
Ota, T. et al. (2006). "Epicardial Atrial Ablation Using a Novel Articulated Robotic Medical Probe Via a Percutaneous Subxiphoid Approach," *National Institute of Health* 1(6):335-340.
Ota, T. et al. (Oct. 2007). "Impact of Beating Heart left Atrial Ablation on Left-sided Heart Mechanics," *The Journal of Thoracic and Cardiovascular Surgery* 134:982-988.
Pennec, P-Y. et al. (2003). "Assessment of Different Procedures for Surgical Left Atrial Appendage Exclusion," *The Annals of Thoracic Surgery* 76:2167-2168.
Perk, G. et al. (Aug. 2009). "Use of Real Time Three-Dimensional Transesophageal Echocardiography in Intracardiac Catheter Based Interventions," *J. Am Soc Echocardiogr* 22(8):865-882.
Pollick C. (Feb. 2000). "Left Atrial Appendage Myopathy," *Chest* 117(2):297-308.
Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.
Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.
Robicsek, F. (1987). "Closed-Chest Decannulation of Transthoracically Inserted Aortic Balloon Catheter without Grafting," *Journal of Cardiac Surgery* 2(2):327-329.
Ross, J. Jr. et al. (Jun. 3, 2008). "Transseptal Left Heart Catheterization: A 50-Year Odyssey," *Journal of the American College of Cardiology* 51(22):2107-2115.
Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.
Ruchat, P. et al. (2002). "Off-pump Epicardial Compartmentalization for Ablation of Atrial Fibrillation," *Interactive Cardio Vascular and Thoracic Surgery* 1:55-57.
Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.
Sapp, J. et al. (Dec. 2001). "Electrophysiology and Anatomic Characterization of an Epicardial Accessory Pathway," *Journal of Cardiovascular Electrophysiology* 12(12):1411-1414.
Scharf, C. et al. (2005). "Catheter Ablation for Atrial Fibrillation: Pathophysiology, Techniques, Results and Current Indications," *Continuous Medical Education* 8:53-61.
Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.

Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.
Schneider, B. et al. (2005, e-pub. Aug. 22, 2005). "Surgical Closure of the Left Atrial Appendage—A Beneficial Procedure?" *Cardiology* 104:127-132.
Schweikert, R.A. et al. (Sep. 16, 2003). "Percutaneous Pericardial Instrumentation for Endo-Epicardial Mapping of Previously Failed Ablation," *Circulation* 108:1329-1335.
Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.
Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.
Sengupta, P.P. et al. (2005). "Transoesophageal Echocardiography," *Heart* 91:541-547.
Sharada, K. et al. (2005). "Non-Surgical Transpericardial Catheter Ablation of Post-Infarction Ventricular Tachycardia," *Indian Heart J* 57:58-61.
Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.
Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.
Smith, P.W. et al. (Nov. 1956). "Diagnosis of Mitral Regurgitation by Cardioangiography," *Circulation* 14:847-853.
Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.
Sosa, E. et al. (1996). "A New Technique to Perform Epicardial Mapping in the EP Laboratory," *J. Cardiovasc. Electrophysiol.* 7(6):531-536.
Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.
Sosa, E. et al. (Dec. 14, 1999). "Different Ways of Approaching the Normal Pericardial Space," *Circulation* 100(24):e115-e116.
Sosa, E. et al. (Jul. 15, 2002). "Gaining Access to the Pericardial Space," *The American Journal of Cardiology* 90:203-204.
Sosa, E. et al. (Apr. 2005). "Epicardial Mapping and Ablation Techniques to Control Centricular Tachycardia," *Journal of Cardiovasc. Electrphsiol.* 16(4):449-452.
Sparks, P.B. et al. (2001). "Is Atrial Flutter a Risk Factor for Stroke?" *Journal of the American College of Cardiology* 38(3):785-788.
Spodick, D.H. (Nov. 1970). "Medical History of the Pericardium," *The American Journal of Cardiology* 26:447-454.
Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.
Stewart, S. (1974). "Placement of the Sutureless Epicardial Pacemaker Lead by the Subxiphoid Approach," *Ann. Of Thoracic Surg.* 18(3):308-313.
Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.
Stokes, K. (Jun. 1990). "Implantable Pacing Lead Technology," *IEEE Engineering in Medicine and Biology* pp. 43-49.
Stöllberger, C. et al. (2000). "Is the Left Atrial Appendage Our Most Lethal Attachment?" *European Journal of Cardio-Thoracic Surgery* 18:625-626.
Stöllberger, C. et al. (Dec. 2003). "Elimination of the Left Atrial Appendage To Prevent Stroke or Embolism?: Anatomic, Physiologic, and Pathophysiologic Considerations," 124(6):2356-2362.

(56) References Cited

OTHER PUBLICATIONS

Stöllberger, C. et al. (2006). "Stroke Prevention by Means of Epicardial Occlusion of the Left Atrial Appendage," *Journal of Thoracic and Cardiovascular Surgery* 132(1):207-208.
Stöllberger, C. et al. (2007). "Arguments Against Left Atrial Appendage Occlusion for Stroke Prevention," *Stroke* 38:e77.
Stöllberger, C. et al. (2007). "Leave the Left Atrial Appendage Untouched for Stroke Prevention!" *Journal of Thoracic and Cardiovascular Surgery* 134(2):549-550.
Su, P. et al. (Sep. 2008, e-pub. May 8, 2007). "Occluding the Left Atrial Appendage: Anatomical Considerations," *Heart* 94(9):1166-1170.
Subramanian, V.A. (Jun. 1997). "Less Invasive Arterial CABG on a Beating Heart," *Ann. Thorac. Surg.* 63(6 Suppl.):S68-S71.
Subramanian, V.A. et al. (Dec. 1997). "Minimally Invasive Direct Coronary Artery Bypass Grafting: two-Year Clinical Experience," *Ann. Thorac. Surg.* 64(6):1648-1653, Abstract Only.
Suehiro, S. et al. (1996). "Echocardiography-Guided Pericardiocentesis With a Needle Attached to a Probe," *Ann. Thoracic Surg.* 61:741-742.
Sun, F. et al. (Feb. 2006). "Subxiphoid Access to Normal Pericardium with Micropuncture Set: Technical Feasibility Study in Pigs," *Radiology* 238(2):719-724.
Szili-Torok, T. et al. (2001). "Transseptal Left heart Catheterisation Guided by Intracardiac Echocardiography," *Heart* 86:e11-e15.
Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.
Tomar, M. et al. (Jul.-Aug. 2006). "Transcatheter Closure of Fossa Ovalis Atrial Septal Defect: A Single Institutional Experience," *Indian Heart Journal* 58(4):325-329.
Troughton, R.W. et al. (Feb. 28, 2004). "Pericarditis," *The Lancet* 363:717-727.
Ulicny K.S. et al. (Jun. 1992). "Conjoined Subrectus Pocket for Permanent Pacemaker Placement in the Neonate," *Ann Thorac Surg.* 53(6):1130-1131, Abstract Only.
Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.
Von Korn, H. et al. (2006). "Simultaneous Combined Interventional Percutaneous Left Atrial Auricle and Atrial Septal Defect Closure," *Heart* 92:1462.
Wang, T.J. et al. (Aug. 27, 2003). "A Risk Score for Predicting Stroke or Death in Individuals With New-Onset Atrial Fibrillation in the Community," *American Medical Association* 290(8):1049-1056.
Watkins, L. et al. (Nov. 1982). "Implantation of the Automatic Defibrillator: The Subxiphoid Approach," *Ann. of Thoracic Surg.* 34(5):515-520.
W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.
Wolber, T. et al. (Jan. 2007). "Potential Interference of Small Neodymium Magnets with Cardiac pacemakers and Implantable Cardioverter-defibrillators," *Heart Rhythm* 4(1):1-4.
Wolf, P.A. et al. (Oct. 1978). "Epidemiologic Assessment of Chronic Atrial Fibrillation and Risk of Stroke: The Fiamingham Study," *Neurology* 28:973-977.
Wolf, P.A. et al. (Aug. 1991). "Atrial Fibrillation as an Independent Risk Factor For Stroke: The Framingham Study," *Stroke* 22(8):983-988.
Wolf, P.A. et al. (Feb. 9, 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.
Wood, M.A. (Jan. 2006). "Percutaneous Pericardial Instrumentation in the Electrophysiology Laboratory: A Case of Need," *Heart Rhythm* 3(1):11-12.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion In Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.
Extended European Search Report dated Jul. 10, 2015, for European Patent Application No. 15153029.2, filed on Mar. 25, 2008, 6 pages.
Extended European Search Report dated Feb. 10, 2017, for EP Application No. 10 759 425.1, filed on Apr. 1, 2010, 7 pages.
Extended European Search Report dated Oct. 30, 2017, for EP Application No. 11 769 218.6, filed on Apr. 13, 2011, 11 pages.
International Search Report dated May 19, 2008, for PCT Application No. PCT/US06/013459, filed on Apr. 7, 2006, 1 page.
International Search Report dated Feb. 27, 2007, for PCT Application No. PCT/US2008/003938, filed on Mar. 25, 2008, 5 pages.
International Search Report dated Jul. 30, 2010, for PCT Application No. PCT/US2008/076703, filed on Sep. 17, 2008, 2 pages.
International Search Report dated Jun. 1, 2010, for PCT Application No. PCT/US2010/029668, filed on Apr. 1, 2010, 2 pages.
Supplementary Search Report dated Mar. 14, 2011, for EP Application No. 04 794 730.4, filed on Oct. 11, 2004, 4 pages.
Written Opinion dated May 19, 2008, for PCT Application No. PCT/US06/013459, filed on Apr. 7, 2006, 6 pages.
Written Opinion of the International Searching Authority dated Feb. 27, 2007, for PCT Application No. PCT/US2008/003938, filed on Mar. 25, 2008, 10 pages.
Written Opinion of the International Searching Authority dated Jul. 30, 2010, for PCT Application No. PCT/US2008/076703, filed on Sep. 17, 2008, 8 pages.
Written Opinion of the International Searching Authority dated Jun. 1, 2010, for PCT Application No. PCT/US2010/029668, filed on Apr. 1, 2010, 8 pages.
Non-Final Office Action dated Mar. 13, 2008 for U.S. Appl. No. 10/963,371, filed Oct. 11, 2004, 13 pages.
Non-Final Office Action dated Aug. 6, 2008 for U.S. Appl. No. 10/963,371, filed Oct. 11, 2004, 14 pages.
Final Office Action dated Jun. 22, 2009, for U.S. Appl. No. 10/963,371, filed Oct. 11, 2004, 11 pages.
Notice of Allowance dated Sep. 17, 2010, for U.S. Appl. No. 10/963,371, filed Oct. 11, 2004, 7 pages.
Non-Final Office Action dated Jun. 26, 2009, for U.S. Appl. No. 11/600,671, filed Nov. 15, 2006, 9 pages.
Final Office Action dated Apr. 14, 2010, for U.S. Appl. No. 11/600,671, filed Nov. 15, 2006, 7 pages.
Notice of Allowance dated Sep. 17, 2010, for U.S. Appl. No. 11/600,671, filed Nov. 15, 2006, 7 pages.
Non-Final Office Action dated Jul. 22, 2010, for U.S. Appl. No. 12/037,802, filed Feb. 26, 2008, 10 pages.
Final Office Action dated Apr. 26, 2011, for U.S. Appl. No. 12/037,802, filed Feb. 26, 2008, 9 pages.

(56) References Cited

OTHER PUBLICATIONS

Non-Final Office Action dated Jan. 16, 2013, for U.S. Appl. No. 12/037,802, filed Feb. 26, 2008, 10 pages.
Final Office Action dated Nov. 8, 2013, for U.S. Appl. No. 12/037,802, filed Feb. 26, 2008, 15 pages.
Notice of Allowance dated Apr. 3, 2014, for U.S. Appl. No. 12/037,802, filed Feb. 26, 2008, 8 pages.
Non-Final Office Action dated Mar. 7, 2012, for U.S. Appl. No. 12/124,023, filed May 20, 2008, 13 pages.
Final Office Action dated Oct. 18, 2012, for U.S. Appl. No. 12/124,023, filed May 20, 2008, 15 pages.
Non-Final Office Action dated May 31, 2013, for U.S. Appl. No. 12/124,023, filed May 20, 2008, 14 pages.
Non-Final Office Action dated May 4, 2015, for U.S. Appl. No. 12/124,023, filed May 20, 2008, 8 pages.
Notice of Allowance dated Oct. 21, 2015, for U.S. Appl. No. 12/124,023, filed May 20, 2008, 9 pages.
Non-Final Office Action dated Dec. 30, 2009, for U.S. Appl. No. 11/400,714, filed Apr. 7, 2006, 8 pages.
Final Office Action dated Jul. 21, 2010, for U.S. Appl. No. 11/400,714, filed Apr. 7, 2006, 10 pages.
Notice of Allowance dated Nov. 24, 2010, for U.S. Appl. No. 11/400,714, filed Apr. 7, 2006, 8 pages.
Non-Final Office Action dated Dec. 22, 2011, for U.S. Appl. No. 13/033,532, filed Feb. 23, 2011, 8 pages.
Final Office Action dated Jul. 11, 2012, for U.S. Appl. No. 13/033,532, filed Feb. 23, 2011, 8 pages.
Final Office Action dated Jun. 8, 2017, for U.S. Appl. No. 14/625,540, filed Feb. 18, 2015, 14 pages.
Non-Final Office Action dated Apr. 2, 2014, for U.S. Appl. No. 13/033,532, filed Feb. 23, 2011, 8 pages.
Final Office Action dated Aug. 12, 2014, for U.S. Appl. No. 13/033,532, filed Feb. 23, 2011, 6 pages.
Non-Final Office Action dated Oct. 28, 2015, for U.S. Appl. No. 13/033,532, filed Feb. 23, 2011, 9 pages.
Final Office Action dated Apr. 1, 2016, for U.S. Appl. No. 13/033,532, filed Feb. 23, 2011, 8 pages.
Non-Final Office Action dated Nov. 15, 2010, for U.S. Appl. No. 12/055,213, filed Mar. 25, 2008, 18 pages.
Non-Final Office Action dated Apr. 28, 2011, for U.S. Appl. No. 12/055,213, filed Mar. 25, 2008, 20 pages.
Final Office Action dated Oct. 28, 2011, for U.S. Appl. No. 12/055,213, filed Mar. 25, 2008, 15 pages.
Non-Final Office Action dated Sep. 18, 2013, for U.S. Appl. No. 12/055,213, filed Mar. 25, 2008, 15 pages.
Notice of Allowance dated Mar. 4, 2014, for U.S. Appl. No. 12/055,213, filed Mar. 25, 2008, 9 pages.
Non-Final Office Action dated Oct. 27, 2011, for U.S. Appl. No. 12/363,359, filed Jan. 30, 2009, 11 pages.
Final Office Action dated May 4, 2012, for U.S. Appl. No. 12/363,359, filed Jan. 30, 2009, 10 pages.
Non-Final Office Action dated Jun. 17, 2014, for U.S. Appl. No. 12/363,359, filed Jan. 30, 2009, 7 pages.
Final Office Action dated Nov. 14, 2014, for U.S. Appl. No. 12/363,359, filed Jan. 30, 2009, 10 pages.
Non-Final Office Action dated Sep. 10, 2015, for U.S. Appl. No. 12/363,359, filed Jan. 30, 2009, 13 pages.
Final Office Action dated Mar. 17, 2016, for U.S. Appl. No. 12/363,359, filed Jan. 30, 2009, 10 pages.
Non-Final Office Action dated Nov. 9, 2011, for U.S. Appl. No. 12/363,381, filed Jan. 30, 2009, 10 pages.
Final Office Action dated May 16, 2012, for U.S. Appl. No. 12/363,381, filed Jan. 30, 2009, 8 pages.
Notice of Allowance dated Apr. 1, 2014, for U.S. Appl. No. 12/363,381, filed Jan. 30, 2009, 9 pages.
Notice of Allowance dated Dec. 29, 2014, for U.S. Appl. No. 12/363,381, filed Jan. 30, 2009, 9 pages.
Non-Final Office Action dated Feb. 17, 2011, for U.S. Appl. No. 12/212,511, filed Sep. 17, 2008, 14 pages.
Final Office Action dated Sep. 20, 2011, for U.S. Appl. No. 12/212,511, filed Sep. 17, 2008, 8 pages.
Non-Final Office Action dated Apr. 2, 2012, for U.S. Appl. No. 12/212,511, filed Sep. 17, 2008, 5 pages.
Final Office Action dated Jul. 24, 2012, for U.S. Appl. No. 12/212,511, filed Sep. 17, 2008, 6 pages.
Notice of Allowance dated Feb. 22, 2013, for U.S. Appl. No. 12/212,511, filed Sep. 17, 2008, 8 pages.
Notice of Allowance dated Mar. 18, 2013, for U.S. Appl. No. 12/212,511, filed Sep. 17, 2008, 6 pages.
Non-Final Office Action dated Mar. 29, 2013, for U.S. Appl. No. 12/752,873, filed Apr. 1, 2010, 16 pages.
Non-Final Office Action dated Dec. 2, 2016, for U.S. Appl. No. 14/625,540, filed Feb. 18, 2015, 20 pages.
Final Office Action dated Jan. 13, 2014, for U.S. Appl. No. 12/752,873, filed Apr. 1, 2010, 10 pages.
Non-Final Office Action dated Nov. 10, 2014, for U.S. Appl. No. 12/752,873, filed Apr. 1, 2010, 10 pages.
Notice of Allowance dated Jul. 22, 2015, for U.S. Appl. No. 12/752,873, filed Apr. 1, 2010, 8 pages.
Non-Final Office Action dated Feb. 5, 2014 for U.S. Appl. No. 13/086,389, filed Apr. 13, 2011, 16 pages.
Non-Final Office Action dated Jan. 15, 2015, for U.S. Appl. No. 13/086,389, filed Apr. 13, 2011, 16 pages.
Non-Final Office Action dated May 3, 2013, for U.S. Appl. No. 13/086,390, filed Apr. 13, 2011, 10 pages.
Final Office Action dated Oct. 22, 2013, for U.S. Appl. No. 13/086,390, filed Apr. 13, 2011, 6 pages.
Notice of Allowance dated Mar. 20, 2014 for U.S. Appl. No. 13/086,390, filed Apr. 13, 2011, 8 pages.
Non-Final Office Action dated Dec. 2, 2015, for U.S. Appl. No. 14/309,835, filed Jun. 19, 2014, 8 pages.
Non-Final Office Action dated Mar. 31, 2015, for U.S. Appl. No. 13/490,919, filed Jun. 7, 2012, 14 pages.
Final Office Action dated Nov. 18, 2015, for U.S. Appl. No. 13/490,919, filed Jun. 7, 2012, 10 pages.
Notice of Allowance dated Apr. 11, 2016, for U.S. Appl. No. 14/195,797, filed Mar. 3, 2014, 14 pages.
Notice of Allowance dated Jul. 19, 2016, for U.S. Appl. No. 13/490,919, filed Jun. 7, 2012, 10 pages.
Partial European Search Report dated Dec. 8, 2017, for EP Application No. 17 166 951.8, filed on Sep. 17, 2008, 16 pages.
Extended European Search Report dated Mar. 15, 2018, for EP Application No. 17 166 951.8, filed on Sep. 17, 2008, 14 pages.
Non-Final Office Action dated Jan. 12, 2018, for U.S. Appl. No. 14/928,836, filed Oct. 30, 2015, 12 pages.
Non-Final Office Action dated Jan. 17, 2018, for U.S. Appl. No. 15/041,777, filed Feb. 11, 2016, 13 pages.
Non-Final Office Action dated Jan. 26, 2018, for U.S. Appl. No. 14/625,540, filed Feb. 18, 2015, 16 pages.
Extended European Search Report dated Feb. 20, 2019, for EP Application No. 18211384.5, 8 pages.
Final Office Action dated Sep. 6, 2018, for U.S. Appl. No. 14/625,540, filed Feb. 18, 2015, 15 pages.
Non-Final Office Action dated May 30, 2019, for U.S. Appl. No. 14/928,836, filed Oct. 30, 2015, 10 pages.
Non-Final Office Action dated Jan. 17, 2018, for U.S. Appl. No. 15/041,777, filed Feb. 11, 2016, 12 pages.
Non-Final Office Action dated Mar. 27, 2019, for U.S. Appl. No. 14/625,540, filed Feb. 18, 2015, 14 pages.
Final Office Action dated Oct. 10, 2018, for U.S. Appl. No. 15/041,777, filed Feb. 11, 2016, 13 pages.
Final Office Action dated Nov. 23, 2018, for U.S. Appl. No. 14/928,836, filed Oct. 30, 2015, 10 pages.
Notice of Allowance dated Feb. 5, 2019, for U.S. Appl. No. 15/041,777, filed Feb. 11, 2016, 9 pages.
Non-Final Office Action dated Mar. 15, 2019, for U.S. Appl. No. 15/634,982, filed Jun. 27, 2017, 10 pages.
United States Patent and Trademark Office, Non-Final Office Action for U.S. Appl. No. 16/375,660, dated Mar. 25, 2021, 13 pages.
United States Patent and Trademark Office, Final Office Action for U.S. Appl. No. 16/375,660, dated Sep. 3, 2021, 9 pages.

(56) References Cited

OTHER PUBLICATIONS

United States Patent and Trademark Office, Notice of Allowance for U.S. Appl. No. 14/625,540, dated Dec. 3, 2020, 10 pages.
United States Patent and Trademark Office, Notice of Allowance for U.S. Appl. No. 16/149,911, dated Dec. 9, 2020, 7 pages.
United States Patent and Trademark Office, Notice of Allowance for U.S. Appl. No. 15/356,521, dated Feb. 9, 2021, 8 pages.
United States Patent and Trademark Office, Notice of Allowance for U.S. Appl. No. 15/634,982, dated Jan. 22, 2021, 5 pages.
United States Patent and Trademark Office, Non-Final Office Action for U.S. Appl. No. 15/634,982, dated Jul. 29, 2020, 9 pages.
United States Patent and Trademark Office, Notice of Allowance for U.S. Appl. No. 15/634,962, dated Jan. 30, 2020, 9 pages.
United States Patent and Trademark Office, Notice of Allowance for U.S. Appl. No. 14/928,836, dated Jul. 13, 2020, 4 pages.
United States Patent and Trademark Office, Notice of Allowance for U.S. Appl. No. 14/928,836, dated Sep. 18, 2020, 4 pages.
United States Patent and Trademark Office, Notice of Allowance for U.S. Appl. No. 15/934,144, filed Mar. 12, 2020, 9 pages.
United States Patent and Trademark Office, Notice of Allowance for U.S. Appl. No. 14/928,836, filed May 28, 2020, 8 pages.
United States Patent and Trademark Office, Notice of Allowance for U.S. Appl. No. 14/928,836, filed Sep. 18, 2020, 3 pages.
United States Patent and Trademark Office, Final Office Action for U.S. Appl. No. 15/713,376, filed Jan. 6, 2020, 8 pages.
United States Patent and Trademark Office, Non-Final Office Action for U.S. Appl. No. 15/713,376, filed Aug. 18, 2020, 8 pages.
United States Patent and Trademark Office, Notice of Allowance for U.S. Appl. No. 15/713,376, filed May 23, 2019, 7 pagesf.
United States Patent and Trademark Office, Notice of Allowance for U.S. Appl. No. 15/713,376, filed Aug. 24, 2021, 7 pages.
Final Office Action dated Mar. 16, 2021 for U.S. Appl. No. 15/713,376, filed Sep. 22, 2017, 9 pages.
Final Office Action dated Oct. 10, 2019, for U.S. Appl. No. 15/634,962, filed Jun. 27, 2017, 12 pages.

* cited by examiner

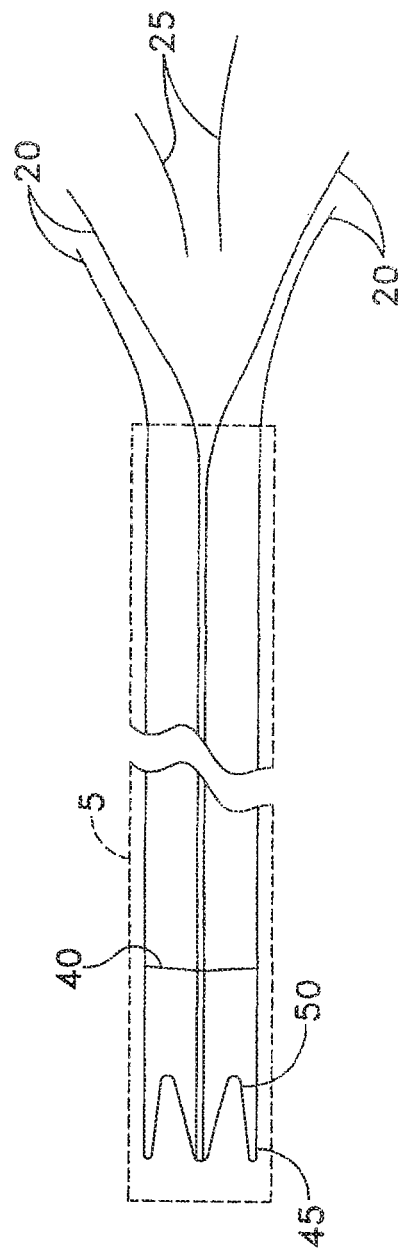
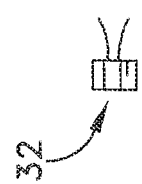
FIG. 11

APPARATUS AND METHOD FOR THE LIGATION OF TISSUE

CROSS-REFERENCE TO RELATED APPLICATIONS

This patent application is a continuation of U.S. patent application Ser. No. 15/041,777, filed on Feb. 11, 2016, which is a continuation of U.S. patent application Ser. No. 12/124,023, filed on May 20, 2008, which issued as U.S. Pat. No. 9,271,819 on Mar. 1, 2016, which is a continuation of U.S. patent application Ser. No. 10/963,371, filed on Oct. 11, 2004, which issued as U.S. Pat. No. 7,846,168 on Dec. 7, 2010, which claims priority to U.S. Provisional Patent Application Ser. No. 60/528,995, filed Dec. 12, 2003, and U.S. Provisional Patent Application Ser. No. 60/510,100 filed on Oct. 9, 2003, each of which is incorporated herein by reference in its entirety.

FIELD OF THE INVENTION

This invention relates to apparatus and methods for ligating tissue, and more particularly to ligating cardiac tissue, and even more particularly to ligating tissue of the left atrium. In one preferred form of the present invention, ligation of the left atrial appendage is effected using a novel apparatus and method.

BACKGROUND OF THE INVENTION

Atrial fibrillation is a common problem that afflicts millions of patients. Unfortunately, atrial fibrillation often results in the formation of a thrombus, or clot, in the appendage of the left atrium. This presents a problem, inasmuch as the thrombus can dislodge and embolize to distant organs, resulting in adverse events such as a stroke. For this reason, most patients with atrial fibrillation are treated with a blood thinner so as to help prevent the formation of a thrombus in the left atrial appendage. Unfortunately, blood thinners pose a substantial health risk in their own right, particularly in the elderly.

An alternative treatment for atrial fibrillation is the ligation of the atrial appendage at its base. This procedure occludes the space in which the thrombus can form, thereby substantially eliminating the risk of forming a clot in the left atrial appendage and/or preventing a clot in the appendage from embolizing. Surgeons have been ligating atrial appendages for years during open surgical procedures. Though effective, this approach requires general anesthesia and surgically opening the chest, which presents additional serious health risks to the patient. Therefore, such open-chest ligation of the atrial appendage is normally restricted to situations where the chest is already being surgically opened for other reasons, or where the patient is at a particularly high risk of embolizing.

Recently, catheter-based techniques have been developed for occluding the left atrial appendage space by placing mechanical devices inside the left atrial appendage. This is done under fluoroscopic and/or echocardiographic guidance without the need for a major chest incision or general anesthesia. Unfortunately, however, these techniques require the implantation of mechanical intracardiac devices which, over time, may result in clot formation, incomplete occluding of the appendage space, infection, etc.

SUMMARY OF THE INVENTION

These and other issues are addressed by the present invention, which comprises a novel catheter-based system which ligates the left atrial appendage (LAA) on the outside of the heart, preferably using a combination of catheters and/or instruments, e.g., a guide catheter positioned inside the left atrial appendage which may assist in locating the left atrial appendage and/or assist in the optimal placement of a ligature on the outside of the appendage, and a ligating catheter and/or instrument outside the heart in the pericardial space to set a ligating element at the neck of the left atrial appendage. As a result, this novel approach provides the advantages of both the open surgical approach (i.e., successful ligation of the atrial appendage on the outside of the heart, while avoiding implantation of a mechanical intracardiac device within the heart), and the catheter-based approach (i.e., providing rapid and reliable access to the left atrial appendage without the need for a major chest incision or general anesthesia).

The apparatus and method described herein are primarily intended to ligate the left atrial appendage, however, the apparatus and method may also be used in the same or similar constructions to stabilize, suture, and/or ligate any other tissue in the body. By way of example but not limitation, using the apparatus and method described herein, other tissues of the heart (such as the left ventricle) may be manipulated so as to alter the conformational geometry of the heart into a more favorable shape.

In another form of the invention, there is provided a guide catheter for use in conjunction with a ligating catheter for ligating tissue, comprising:
a shaft having a distal end; and
an alignment element disposed on the distal end of the shaft, wherein the alignment element interacts with a counterpart alignment element on the ligating catheter so as to facilitate alignment of the ligating catheter with the guide catheter.

In another form of the invention, there is provided a guide catheter for use in conjunction with a ligating catheter for ligating tissue, comprising:
a shaft having a distal end; and
an expandable element connected to the distal end of the shaft, wherein the expandable element is configured to expand to a size corresponding to the interior of the left atrial appendage.

In another form of the invention, there is provided a ligating catheter for ligating tissue, comprising:
a hollow shaft having a distal end;
a ligating subassembly comprising a plurality of expandable arms arranged in an arcuate configuration and releasably supporting a ligating element thereon, the ligating subassembly being slidably received within the hollow shaft and adapted to move between (i) a retracted position wherein the expandable arms are received within the hollow shaft, and (ii) an extended position wherein the expandable arms project from the distal end of the hollow shaft, with the expandable arms holding the ligating element radially outboard of the shaft when the ligating subassembly is in its second position.

In another form of the invention, there is provided a ligating catheter for ligating tissue, comprising:
a hollow shaft having a distal end;
a ligating subassembly comprising a plurality of expandable arms arranged in an arcuate configuration and releasably supporting a ligating element thereon, the ligating subassembly being slidably received within the hollow shaft and adapted to move between (i) a retracted position wherein the expandable arms are received within the hollow shaft, and (ii) an extended position wherein the expandable arms project from the distal end of the hollow shaft, with the expandable arms holding the ligating element radially outboard of the shaft when the ligating subassembly is in its second position;

an alignment element mounted to the shaft, wherein the alignment element interacts with a counterpart alignment element on a guide catheter disposed within the tissue to be ligated; and gripping apparatus for gripping tissue, wherein the gripping apparatus comprises a suction tube mounted to the hollow shaft.

In another form of the invention, there is provided a system for ligating tissue comprising:

a guide catheter comprising:
  a shaft having a distal end; and
  an alignment element disposed on the distal end of the shaft, wherein the alignment element interacts with a counterpart alignment element on a ligating catheter so as to facilitate alignment of the ligating catheter with the guide catheter; and a ligating catheter for ligating tissue, comprising:
  a hollow shaft having a distal end;
  a ligating subassembly comprising a plurality of expandable arms arranged in an arcuate configuration and releasably supporting a ligating element thereon, the ligating subassembly being slidably received within the hollow shaft and adapted to move between (i) a retracted position wherein the expandable arms are received within the hollow shaft, and (ii) an extended position wherein the expandable arms project from the distal end of the hollow shaft, with the expandable arms holding the ligating element radially outboard of the shaft when the ligating subassembly is in its second position; and
  an alignment element mounted to the shaft, wherein the alignment element interacts with counterpart alignment element on the guide catheter when the guide catheter is disposed within the tissue to be ligated.

In another form of the invention, there is provided a system for ligating tissue comprising:

a guide catheter comprising:
  a shaft having a distal end; and
  an alignment element disposed on the distal end of the shaft, wherein the alignment element interacts with a counterpart alignment element on a ligating catheter so as to facilitate alignment of the ligating catheter with the guide catheter; and
  an expandable element connected to the distal end of the shaft, wherein the expandable element is configured to expand to a size corresponding to the interior of the left atrial appendage; and a ligating catheter for ligating tissue, comprising:
  a hollow shaft having a distal end;
  a ligating subassembly comprising a plurality of expandable arms arranged in arcuate configuration and releasably supporting a ligating element thereon, the ligating subassembly being slidably received within the hollow shaft and adapted to move between (i) a retracted position wherein the expandable arms are received within the hollow shaft, and (ii) an extended position wherein the expandable arms project from the distal end of the hollow shaft, with the expandable arms holding the ligating element radially outboard of the shaft when the ligating subassembly is in its second position;
  an alignment element mounted to the shaft, wherein the alignment element interacts with counterpart alignment element on the guide catheter when the guide catheter is disposed within the tissue to be ligated; and
  a gripping apparatus for gripping tissue, wherein the gripping apparatus comprises a suction tube mounted to the hollow shaft.

In another form of the invention, there is provided a method for ligating tissue, comprising:
  positioning a guide catheter within the interior of the tissue to be ligated, wherein the guide catheter comprises an alignment element for interacting with a counterpart alignment element on a ligating catheter;
  advancing a ligating catheter so as to position a ligating element about the tissue to be ligated, wherein the ligating catheter interacts with the alignment element on the guide catheter when positioning the ligating element about the tissue to be sutured; and
  contracting the ligating element about the tissue, whereby to ligate the tissue.

In another form of the invention, there is provided a method for ligating tissue, comprising:
  providing a guide catheter and a ligating catheter, wherein the guide catheter comprises an alignment element for interacting with a counterpart aligning element on the ligating catheter so as to facilitate alignment of the ligating catheter with the guide catheter;
  positioning the guide catheter within the tissue to be ligated;
  using the alignment elements to align the ligating catheter with the guide catheter and about the tissue to be ligated; and
  ligating the tissue with the ligating catheter.

In another form of the invention, there is provided a system for ligating tissue comprising:
  a wire extending from the interior of the left atrial appendage, through the side wall of the left atrial appendage, and out the pericardium;
  a guide catheter slidably mounted on the wire, comprising:
    a shaft having a distal end; and
    an expandable element connected to the distal end of the shaft, wherein the expandable element is configured to expand to a size corresponding to the interior of the left atrial appendage; and
  a ligating catheter for ligating tissue, comprising:
    a hollow shaft having a distal end; and
    a ligating subassembly comprising a plurality of expandable arms arranged in an arcuate configuration and releasably supporting a ligating element thereon, the ligating subassembly being slidably received within the hollow shaft and adapted to move between (i) a retracted position wherein the expandable arms are received within the hollow shaft, and (ii) an extended position wherein the expandable arms project from the distal end of the hollow shaft, with the expandable arms holding the ligating element radially outboard of the shaft when the ligating subassembly is in its second position.

In another form of the invention, there is provided a method for performing a procedure on a body structure, comprising:
  inserting a first device with an alignment element into the body structure;
  positioning a second device outside of the body structure;

aligning the first device with the second device with the alignment element; and performing a procedure on the body structure with the devices.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 11 is a view like that of FIG. 10, except that the ligating element has been severed from the ligating catheter;

DETAILED DESCRIPTION OF THE PREFERRED EMBODIMENTS

Ligating Catheter

Figure 1:
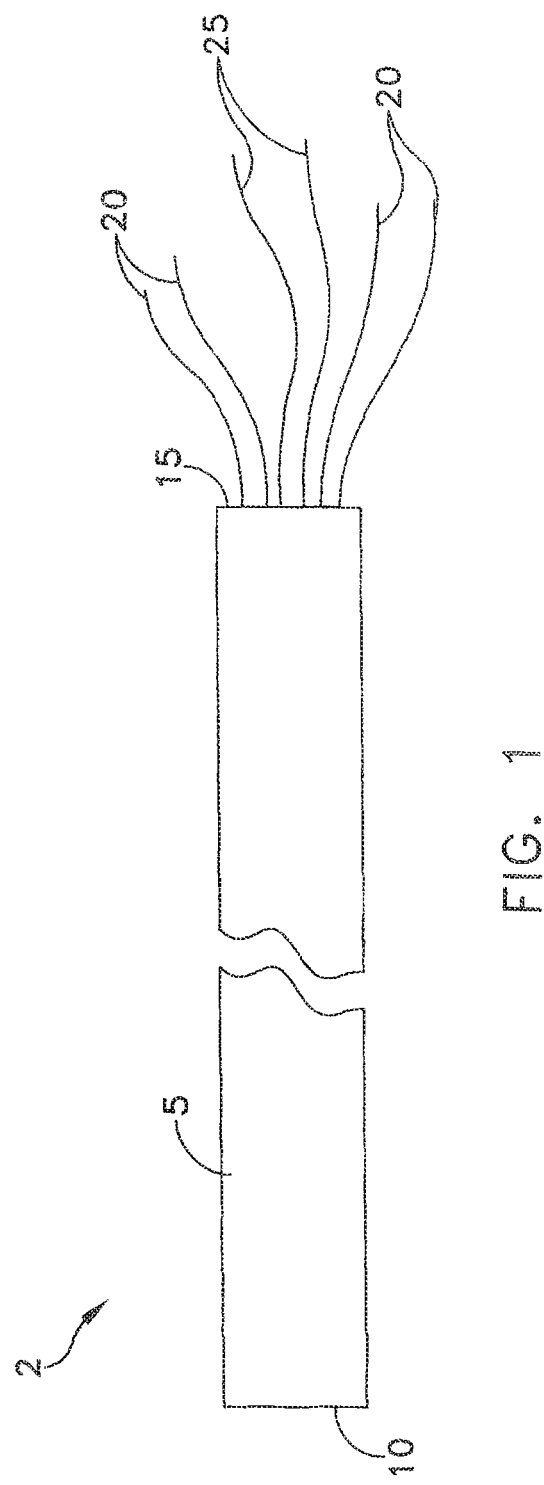
FIG. 1 is a side view of a ligating catheter, with the catheter's ligation subassembly being disposed in a retracted position.

Looking first at FIG. 1, there is shown a ligating catheter 2 formed in accordance with the present invention. Ligating catheter 2 comprises an elongated tube or cylinder 5, having a distal end 10 and a proximal end 15. Exiting from proximal end 15 are one or more advancement/retraction control elements 20, which are connected to the ligation subassembly (not shown in FIG. 1) disposed inside cylinder 5. In the construction shown in FIG. 1, advancement/retraction control elements 20 comprise cables or wires. One or more advancement/retraction control elements 20 are used to advance or withdraw the ligation subassembly (not shown in FIG. 1) disposed inside cylinder 5. In addition to the foregoing, one or more constriction control elements 25 also exit from the proximal end of cylinder 5. Constriction control elements 25 are also connected to the ligation subassembly (not shown in FIG. 1) disposed inside cylinder 5 and are used to tighten or loosen the ligating element (also not shown in FIG. 1) about a portion of the tissue or the like. In the construction shown in FIG. 1, constriction control elements 25 comprise cables or sutures.

Figure 2:
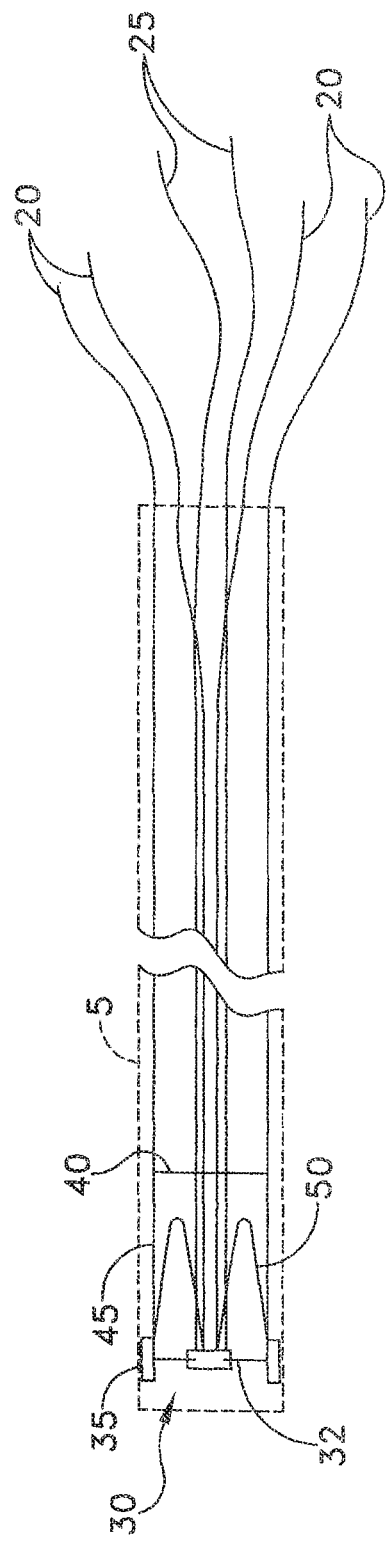
FIG. 2 is a view like that of FIG. 1, except that portions of the ligating catheter have been shown in phantom.

Looking next at FIG. 2, outer cylinder 5 is shown in phantom. FIG. 2 shows the ligation subassembly 30 in an undeployed state, i.e., with ligation subassembly 30 retracted into cylinder 5. Inside cylinder 5, ligation subassembly 30 is shown having a ligating element 32 (e.g., a suture or string) that may be connected to supports or guides (such as felt pledgets or loops 35) which help to grip and protect the tissue which is being ligated. Ligation subassembly 30 also includes supporting structure 40 with struts 45. Felt pledgets 35 are disposed on the distal ends of struts 45. Struts 45 are configured to expand when ligation subassembly 30 is deployed from cylinder 5. In one preferred construction, struts 45 are expanded by connecting them to one another with springs 50, whereby to render struts 45 self-expandable when the struts are advanced out of the distal end of cylinder 5. Ligation subassembly 30 is connected to advancement/retraction control elements 20, whereby the ligation subassembly 30 can be advanced out of, or retracted into, cylinder 5. Furthermore, ligation subassembly 30 is connected to constriction control elements 25, whereby the ligating element 32 can be constricted about a piece of tissue or the like. Advancement/retraction control elements 20, and/or constriction control elements 25, may be connected to an appropriate handle (not shown) for manipulation by a practitioner.

Figure 3:
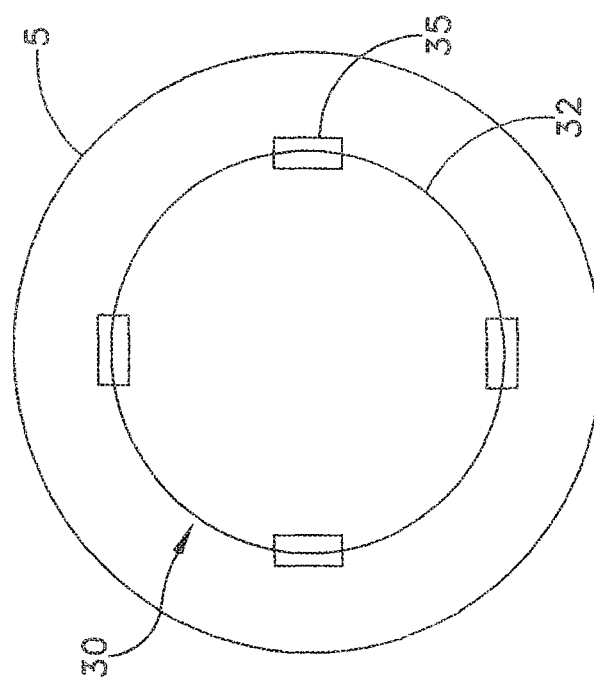
FIG. 3 is an end view of the ligating catheter shown in FIG. 1.

Looking now at FIG. 3, there is shown the distal end 10 of cylinder 5, with the ligation subassembly 30 undeployed within outer cylinder 5, with felt pledgets 35.

Figure 4:
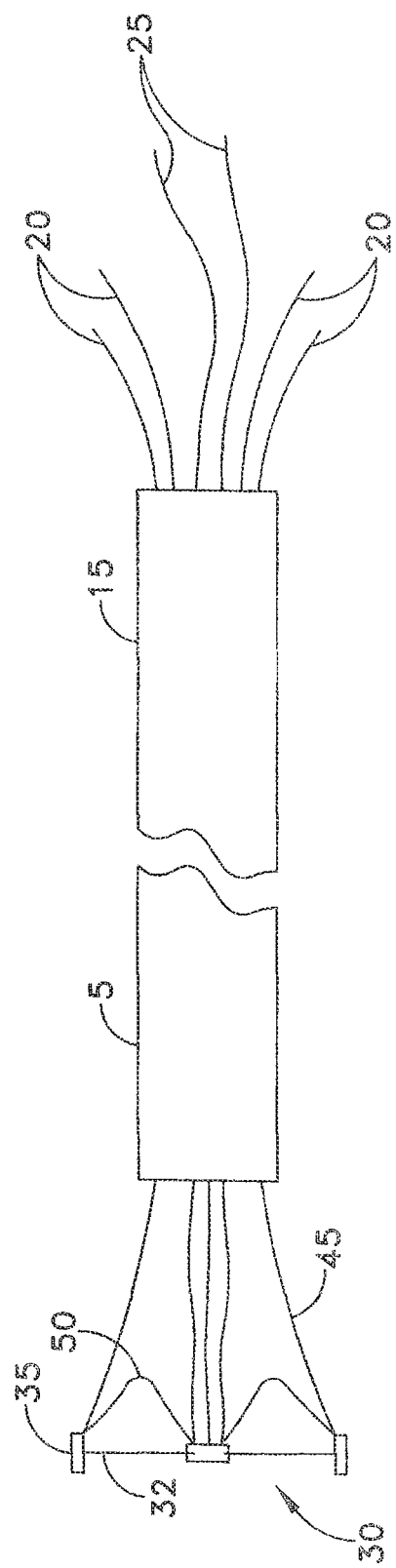
FIG. 4 is a view like that of FIG. 1, except that the catheter's ligation subassembly is shown in an extended position.

Looking next at FIG. 4, a portion of the ligation subassembly 30 is shown advanced out the distal end of the cylinder 5. The ligation subassembly 30 expands as the struts 45 exit the constraining environment of tube 5 and expand away from one another. In the construction shown in FIGS. 1-4, struts 45 expand under the influence of springs 50. Ligation subassembly 30 is connected to constriction control elements 25 which extend beyond proximal end 15 of tube 5 for actuation by the practitioner. Ligation subassembly 30 may be advanced out of the cylinder by pushing on advancement/retraction control elements 20.

Figure 5:
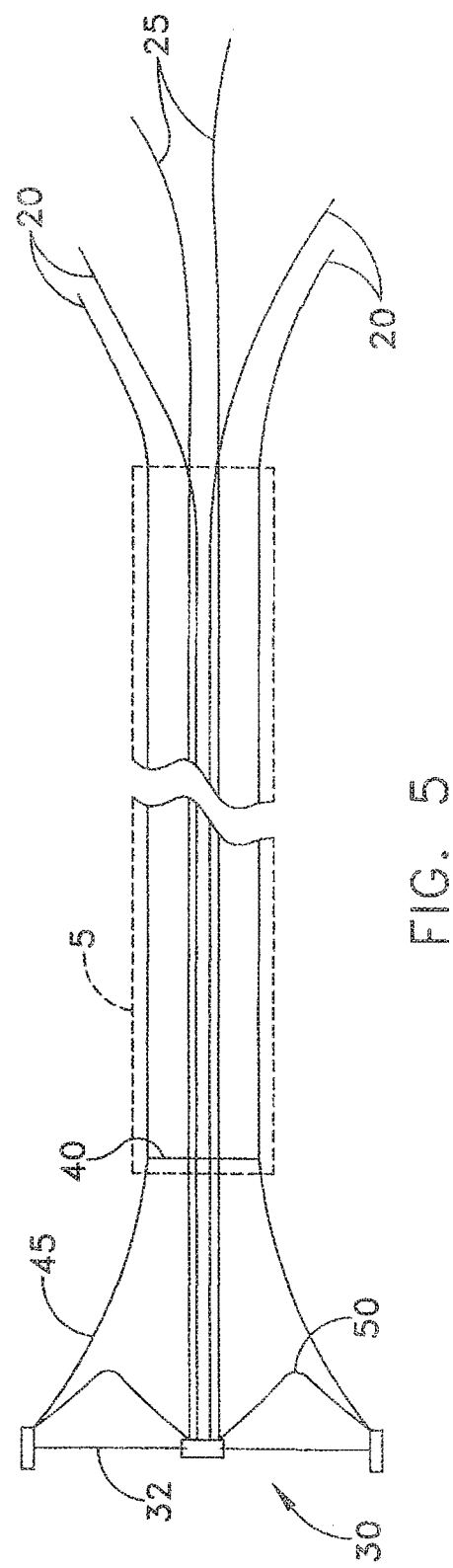
FIG. 5 is a view like that of FIG. 4, except that portions of the ligating catheter have been shown in phantom.

FIG. 5 is similar to FIG. 4, except that the walls of cylinder 5 are shown in phantom, thereby exposing the inner workings of the device. Struts 45 are shown connected to supporting structure 40, e.g., an inner supporting ring 40.

Figure 6:
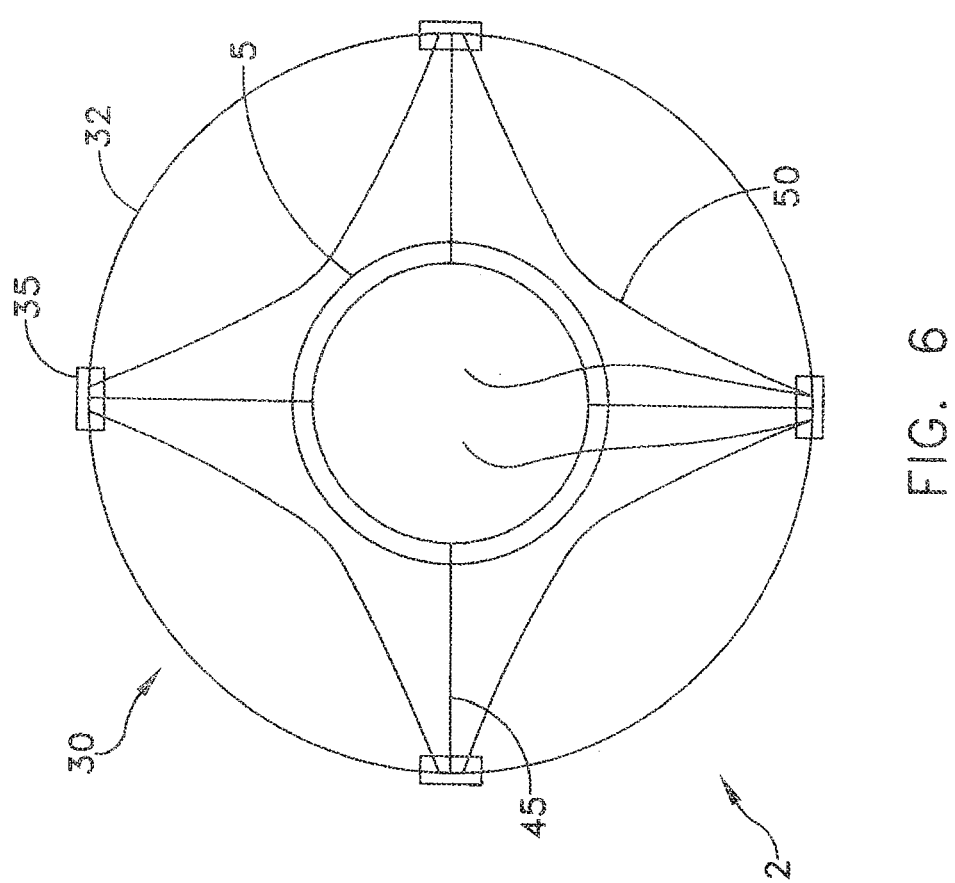
FIG. 6 is an end view of the ligating catheter shown in FIG. 4.

FIG. 6 is a distal end view of the device, showing ligation subassembly 30 advanced out of cylinder 5. Ligation subassembly 30 is expanded radially, with the ligating element 32 following an expanded arcuate path about the distal ends of struts 45, with the proximal ends of ligating element 32 passing up through the center of cylinder 5 for actuation by constriction control elements 25. Thus, ligating element 32 is supported by struts 45 (or other means), struts 45 may be expanded by springs 50 (or by other means), and struts 45 may be supported by supporting structure 40.

Figure 7:
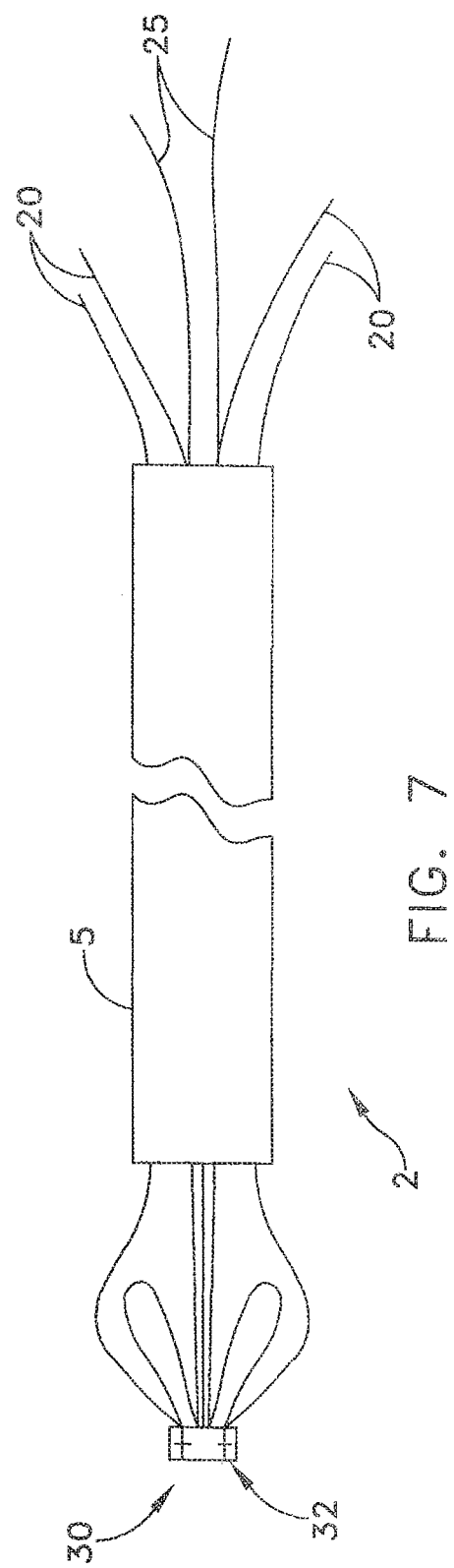
FIG. 7 is a view like that of FIG. 4, but with the ligating element being contracted.

Looking next at FIG. 7, ligating catheter 2 is shown with ligating element 32 contracted. Ligating element 32 may be contracted by pulling on the proximal ends of constriction control elements 25. This actuation causes radial contraction of the ligature loop.

Figure 8:
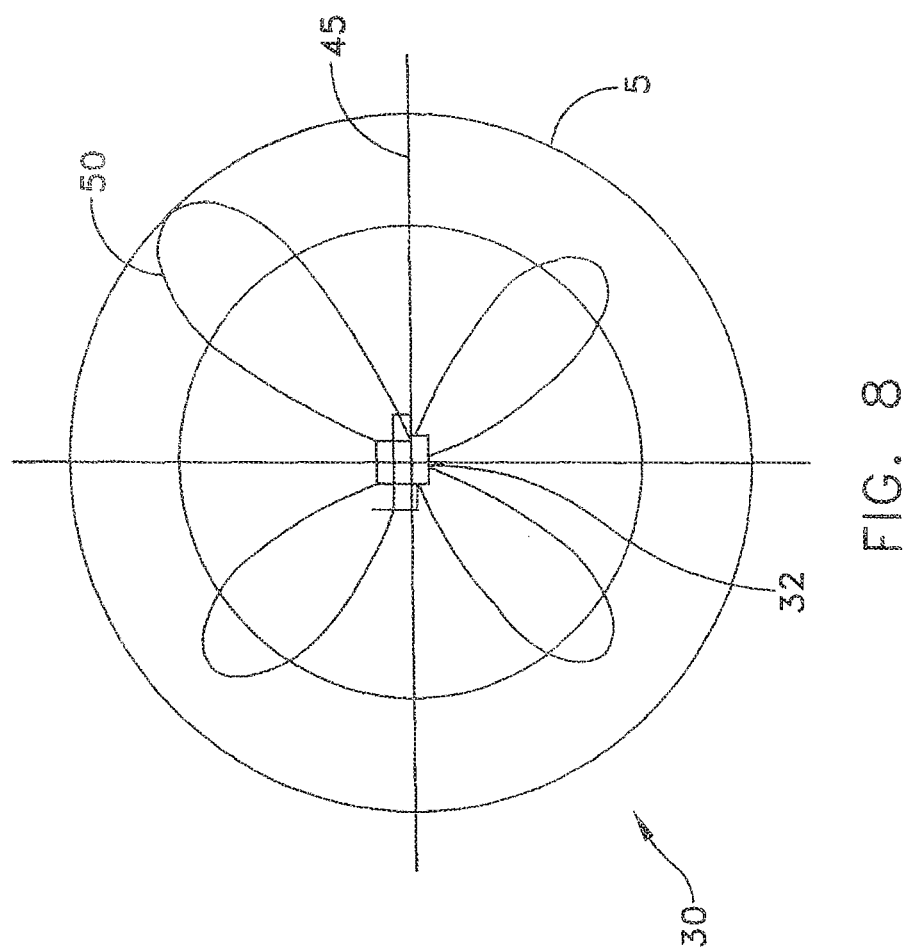
FIG. 8 is an end view of the ligating catheter shown in FIG. 7.

FIG. 8 is a distal end view of the ligating catheter 2 with ligating element 32 contracted. There is radial compression of the ligature loop. Preferably, the inner supporting structure 40 remains unchanged in radial dimension, as does the distal end of the cylinder 5. Preferably, struts 45 and springs 50 collapse as the device is actuated by the practitioner.

Figure 9:
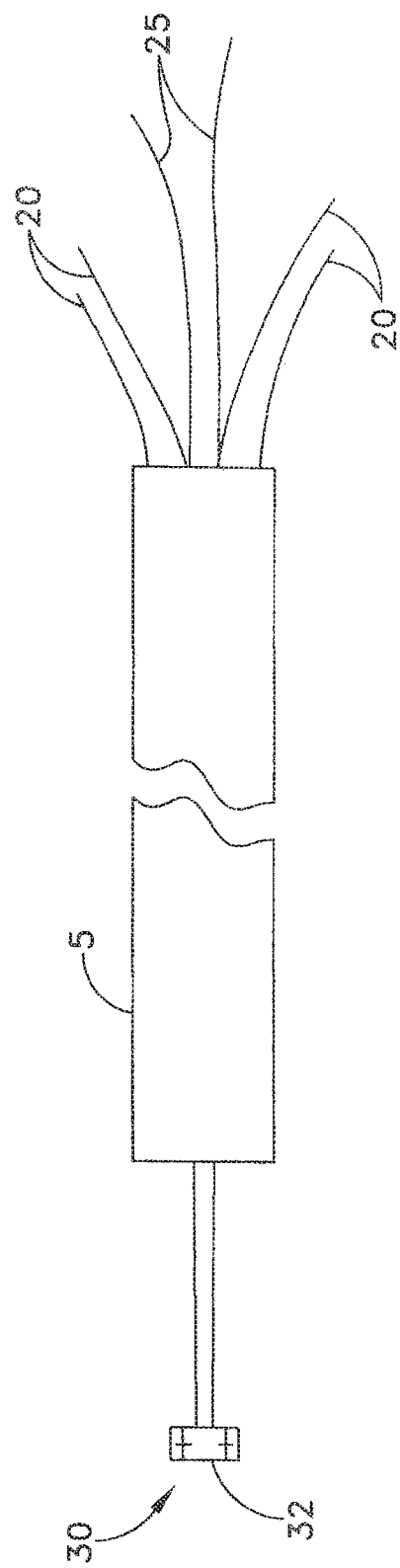
FIG. 9 is a view like that of FIG. 7, but with the catheter's ligation subassembly fully retracted.

FIG. 9 shows struts 45 and springs 50 retracted back into cylinder 5, i.e., by pulling on the advancement/retraction control elements 20. Ligating element 32 remains in place, applying radial compression to any captivated tissue.

Figure 10:
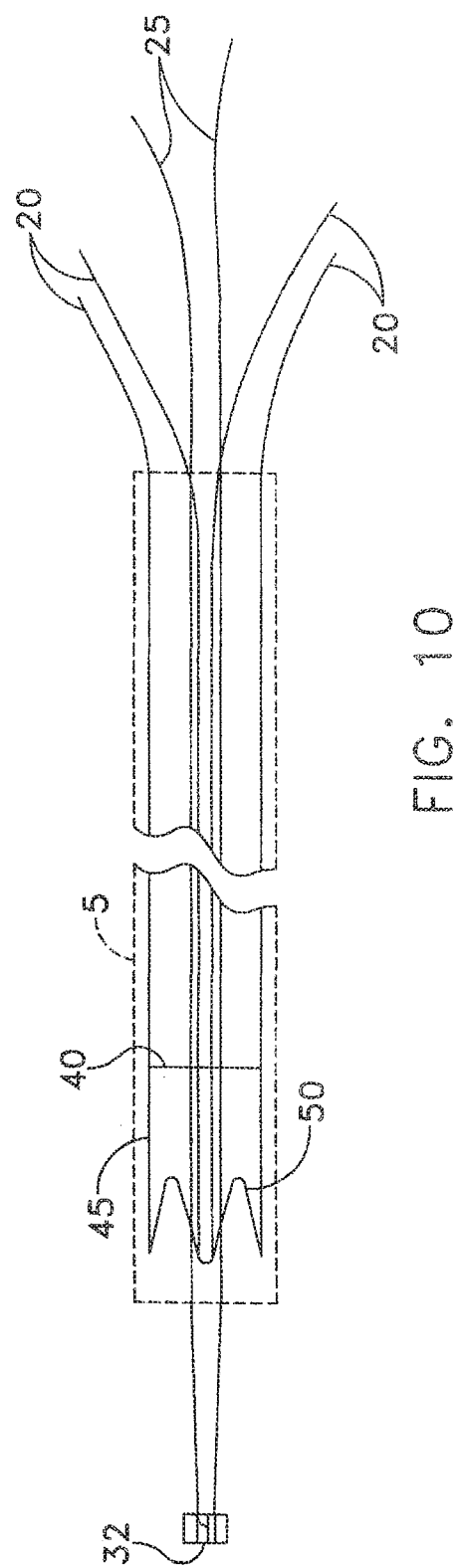
FIG. 10 is a view like that of FIG. 9, except that certain portions of the ligating catheter are shown in phantom.

FIG. 10 is similar to FIG. 9, except that ligating catheter 2 is shown with its cylinder 5 in phantom. Struts 45, springs 50, and supporting structure 40 are shown retracted into cylinder 5.

FIG. 11 shows the ligating element 32 severed from constriction control elements 25.

Guide Catheter

Figure 12:
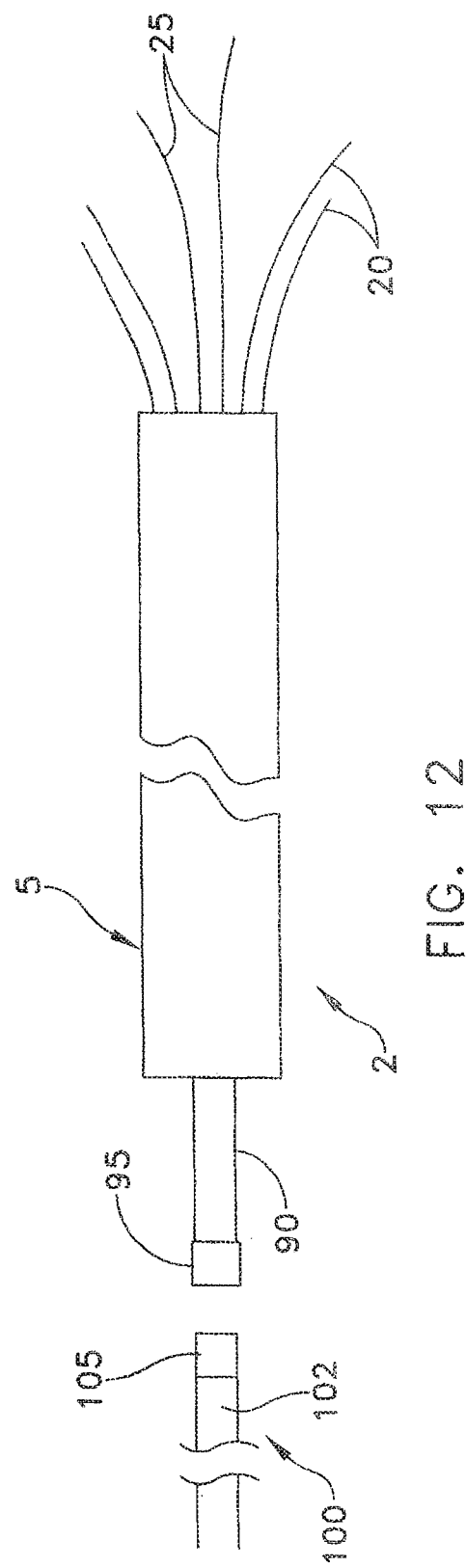
FIG. 12 is a side view showing the ligating catheter in combination with a guide catheter.

FIG. 12 shows the ligating catheter 2 equipped with an alignment element 90. Alignment element 90 is intended for use in aligning ligating catheter 2 with a left atrial appendage or other target structure. In one embodiment of the present invention, alignment element 90 comprises a radio-opaque material, and the device is placed into the desired anatomical position by visualization, e.g., fluoroscopy.

Alternatively, and more preferably, alignment element 90 is intended to work in conjunction with a guide catheter 100, wherein the guide catheter 100 is placed (e.g., endoluminally) within the interior of the left atrial appendage. In this construction, guide catheter 100 also comprises a radio-opaque material, and alignment element 90 and guide catheter 100 are placed in alignment by visualization.

Even more preferably, ligating catheter 2 and guide catheter 100 are provided with physical means (e.g., magnets, male and female connectors, wires and snares, etc.) to facilitate alignment of ligating catheter 2 and guide catheter 100. Thus, in one preferred construction, ligating catheter 2 has its alignment element 90 equipped with a reference magnet 95 at its distal tip. Guide catheter 100 in turn comprises an alignment element 102 having a reference magnet 105 at its distal tip. More particularly, with this preferred construction, ligating catheter 2 has the alignment element 90 which can be extended from the distal end of cylinder 5. On the distal end of alignment element 90 is the reference magnet 95. Alignment element 90 is put into proximity with the guide catheter 100, which has the alignment element 102 with reference magnet 105 mounted on its distal end. When these two alignment elements 90 and 102 are brought into proximity with one another, magnets 95 and 105 cause the alignment elements 90 and 102 to automatically align with one another.

For example, during left atrial appendage ligation, guide catheter 100 is passed endoluminally into the left atrium appendage under visual guidance such as fluoroscopy or ultrasound. The ligating catheter 2 is passed into the pericardium. The alignment element 90 of the ligating catheter is then extended from cylinder 5. Once alignment element 90 is placed into proximity with alignment element 102, magnets 95, 105 cause the two catheters to automatically align with one another, thereby causing ligating catheter 2 to assume a desired position with respect to the left atrial appendage. Then, ligating catheter 2 is utilized as described above to ligate the left atrial appendage.

Figure 13:
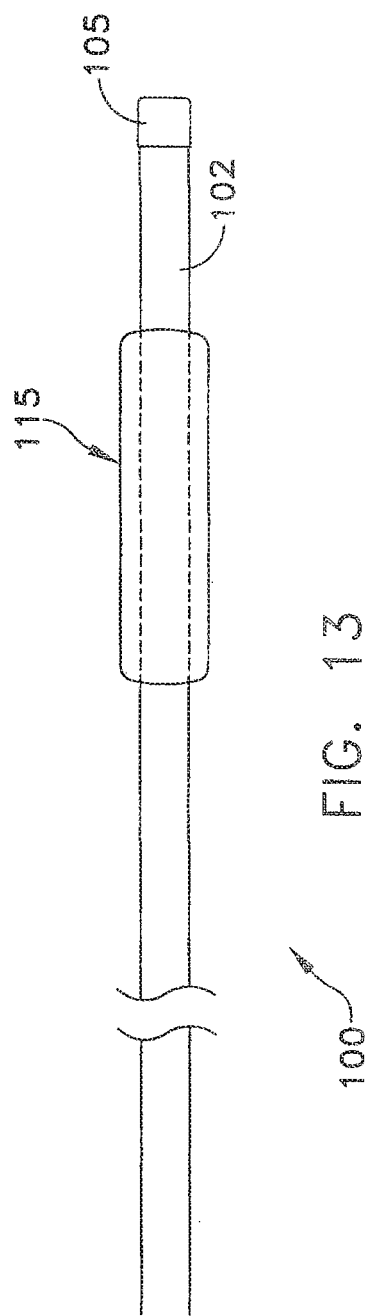
FIG. 13 is a side view of the distal tip of the guide catheter, with the catheter's expanding element being shown in a contracted position.

Looking next at FIG. 13, there is shown a guide catheter 100 which is provided with an expandable element 115. Expandable element 115 is adapted to expand inside the anatomy (e.g., the left atrial appendage) so as to facilitate ligation. As noted above, guide catheter 100 has a magnet 105 mounted to its distal end. It should be noted that expandable element 115 is shown in its non-expanded state in FIG. 13.

Figure 14:
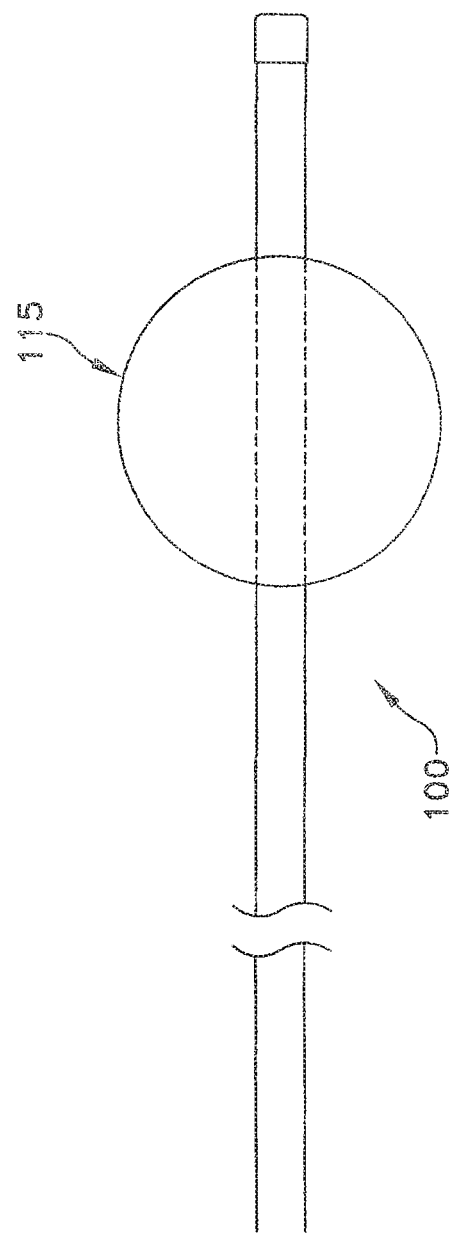
FIG. 14 is a view like that of FIG. 13, except that the catheter's expanding element is shown in an expanded position.

Looking next at FIG. 14, guide catheter 100 is shown with its expandable element 115 in its expanded state.

Figure 15:
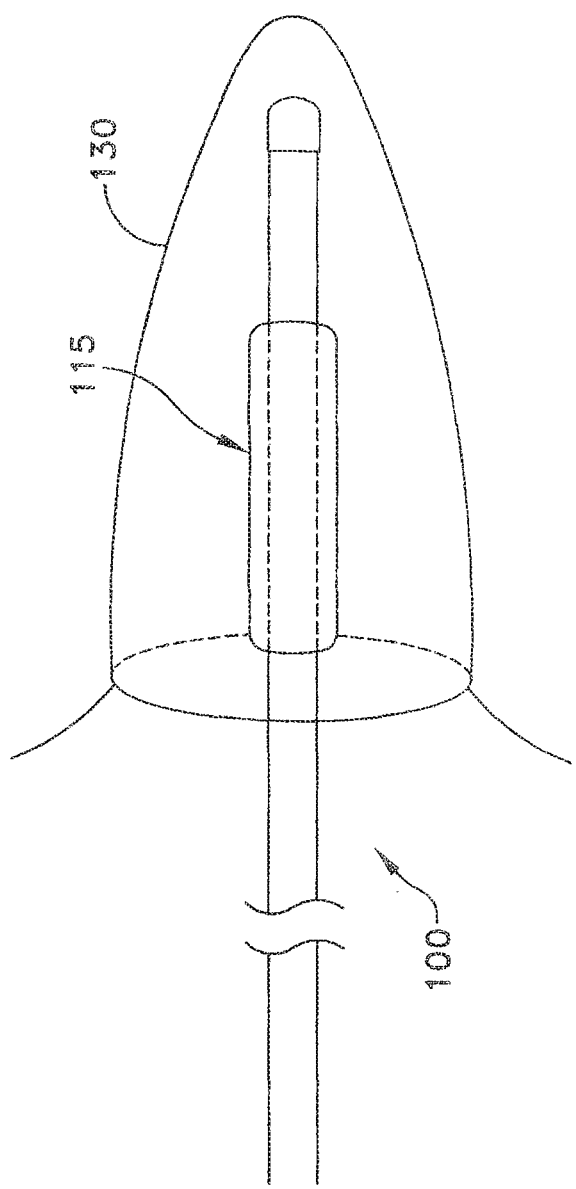
FIG. 15 is a view showing the distal tip of the guide catheter placed within the left atrial appendage, with the catheter's expanding element being shown in a contracted position.

FIG. 15 shows guide catheter 100, with its expandable element 115 not expanded, and with guide catheter 100 disposed in the left atrial appendage 130.

Figure 16:
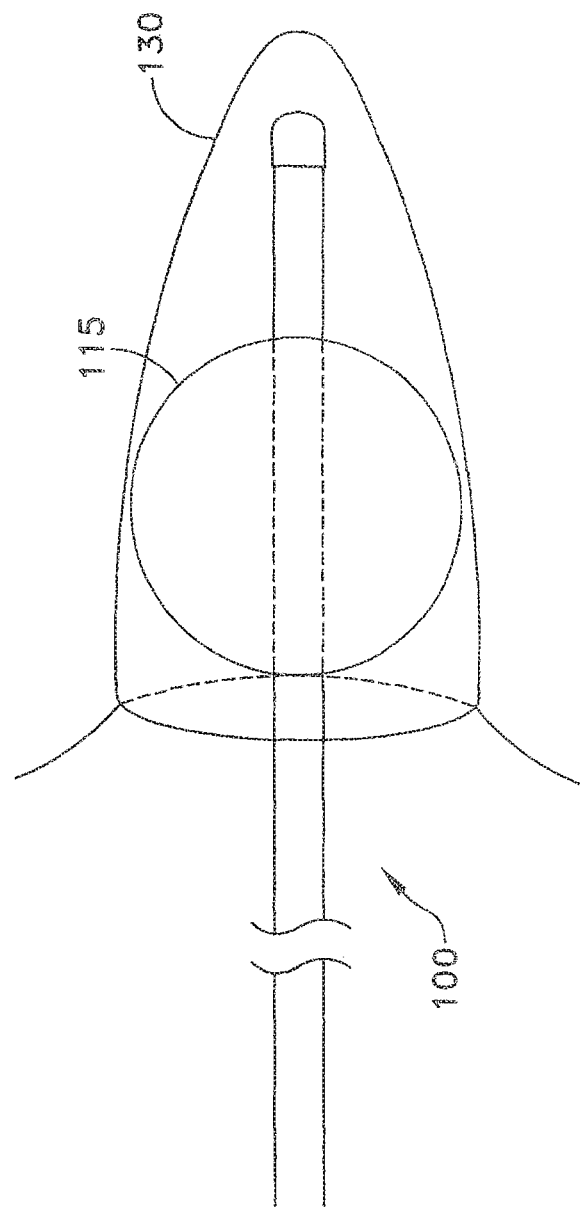
FIG. 16 is a view like that of FIG. 15, except that the catheter's expanding element is shown in an expanded position.

FIG. 16 shows guide catheter 100, with its expandable element 115 expanded, and with guide catheter 100 shown in the left atrial appendage 130. In this respect it should be appreciated when expandable element 115 is in its expanded condition within left atrial appendage 130, expandable element 115 may or may not alter the shape of the recipient tissue, depending on the size of the tissue cavity, the size of the expanded expandable element 115, etc.

Ligating Catheter Used in Conjunction with Guide Catheter

Figure 17:
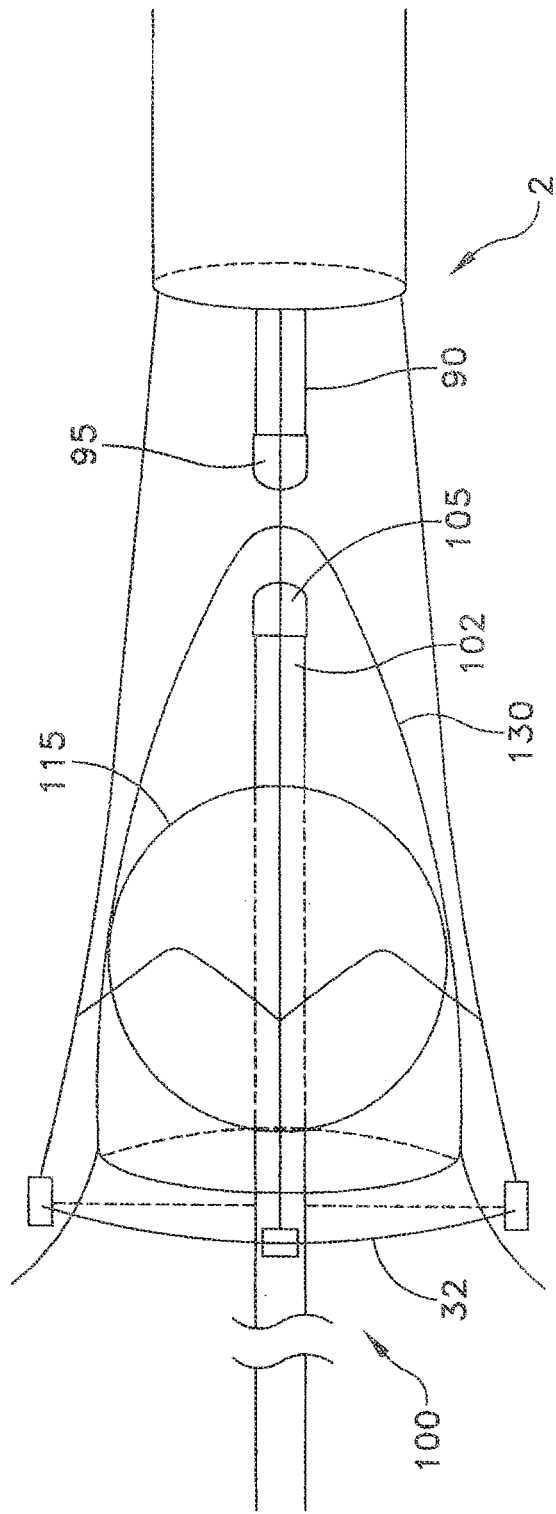
FIG. 17 shows the guide catheter placed within the left atrial appendage, the guide catheter's expanding element placed in its expanded state, and the ligating catheter placed over the left atrial appendage.

FIG. 17 shows guide catheter 100 with its expandable element 115 expanded in the left atrial appendage 130, and with ligating catheter 2 expanded over the left atrial appendage 130. This aligned positioning is facilitated through the use of alignment element 90 on ligating catheter 2 and alignment element 102 on guide catheter 100. More particularly, guide catheter 100 is positioned in the left atrial appendage 130, expandable element 115 is expanded, ligating catheter 2 is positioned in the state depicted in FIGS. 4, 5 and 6 and, using guide elements 90 and 102 to align the apparatus, ligating catheter 2 is slid over the left atrial appendage 130. Guide catheter 100 (inside the left atrial appendage) and ligating catheter 2 are aligned in this preferred construction using magnets 120 and 95, respectively. Significantly, by properly sizing the apparatus vis-à-vis the anatomy, ligating element 32 can be positioned at the neck of the left atrial appendage (and on the atrium side of expandable element 115) when alignment elements 90 and 102 function as described.

Figure 18:
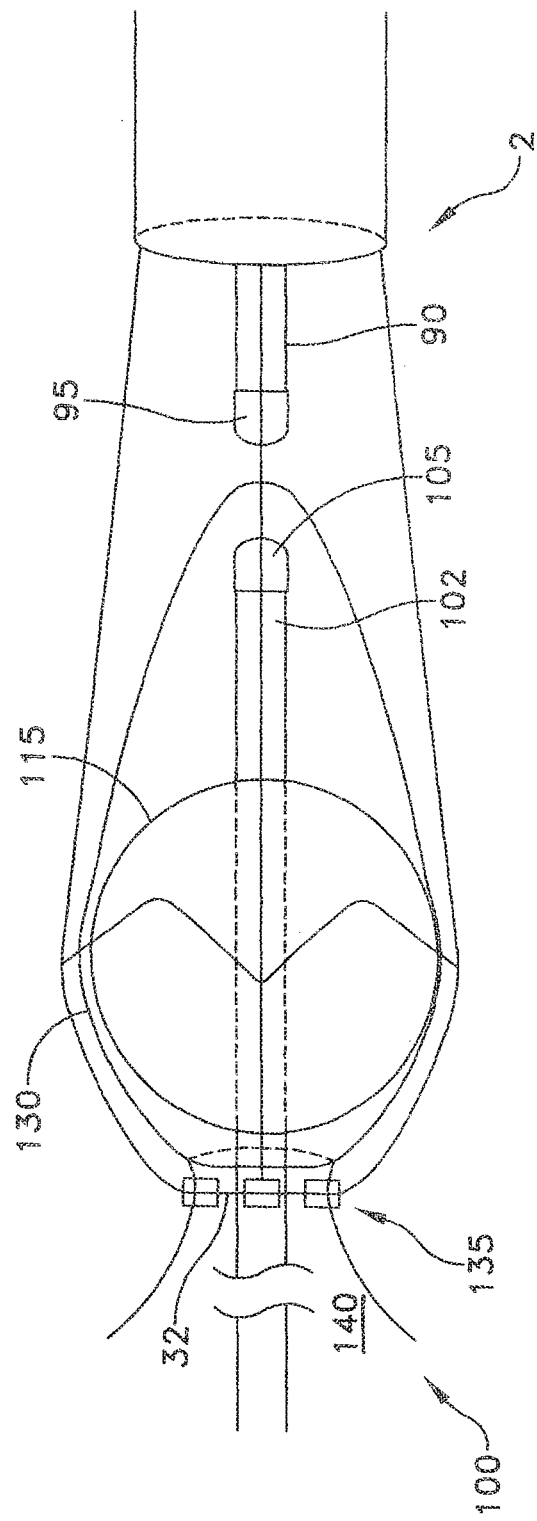
FIG. 18 is a view like that of FIG. 17, except that the ligating catheter has had its ligating element contracted about the neck of the left atrial appendage.

Looking next at FIG. 18, guide catheter 100 is shown in the left atrial appendage 130, with its expandable element 115 in its expanded condition, and ligating catheter 2 is shown actuated as described hereinabove with respect to FIGS. 7 and 8. Due to the relative positioning of the expanded guide catheter 100 within the left atrial appendage 130 while ligating catheter 2 is being actuated, the constricting ligating element 32 is maintained at the neck of the left atrial appendage 130 by the presence of the expandable element 115, thereby helping to ensure proper positioning of the ligating element 32 relative to the anatomy. In other words, the presence of the expandable element 115 inside the left atrial appendage 130 guides ligature 32 into the desired position 135. In the example of ligating the left atrial appendage 130, the desired position 135 is where the left atrial appendage 130 meets the left atrium 140.

Figure 19:
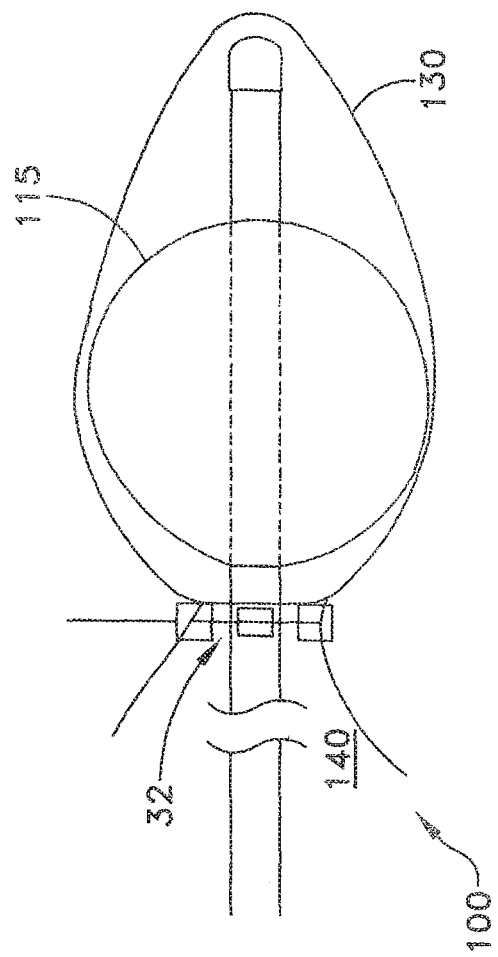
FIG. 19 is a view like that of FIG. 18, except that the ligating catheter has been withdrawn from the surgical site.

Looking next at FIG. 19, the apparatus is shown with guide catheter 100 still in the left atrial appendage 130, but with the ligating catheter 2 withdrawn, leaving the ligating element 32 deployed at the neck of the left atrial appendage 130.

Figure 20:
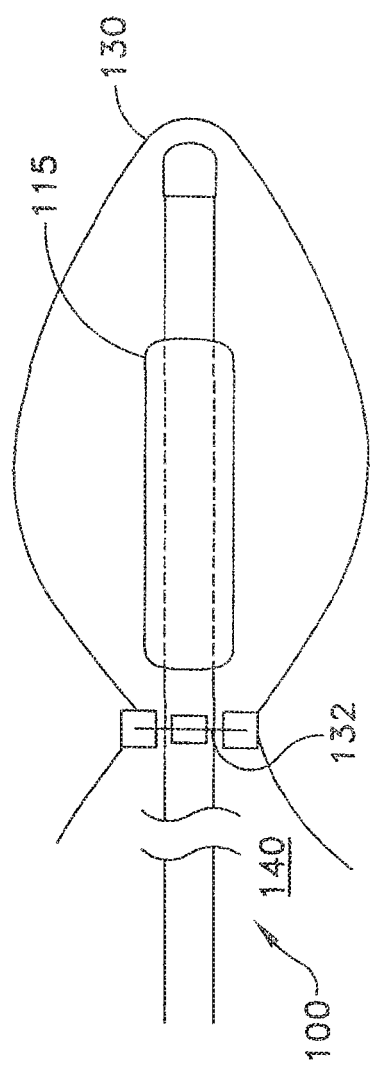
FIG. 20 is a view like that of FIG. 19, except that the guide catheter's expanding element has been contracted.

In FIG. 20, guide catheter 100 has had its expandable element 115 returned to its unexpanded condition.

Figure 21:
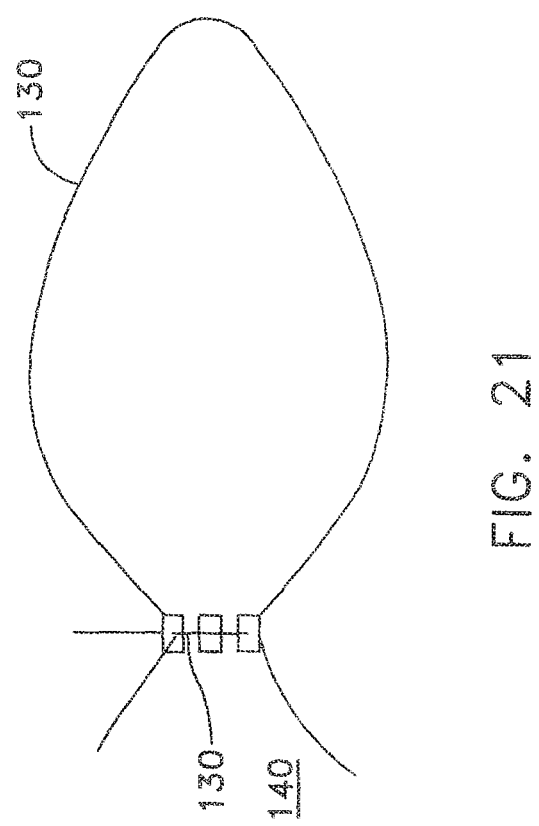
FIG. 21 is a view like that of FIG. 20, except that the guide catheter has been withdrawn from the left atrial appendage.

Looking next at FIG. 21, the left atrial appendage 130 is shown with guide catheter 100 removed from the interior of the left atrial appendage, leaving ligating element 32 at the location where the left atrial appendage 130 meets the left atrium 140, thereby effectively ligating the left atrial appendage from atrium 140.

One Preferred Form of Use

Figure 22:
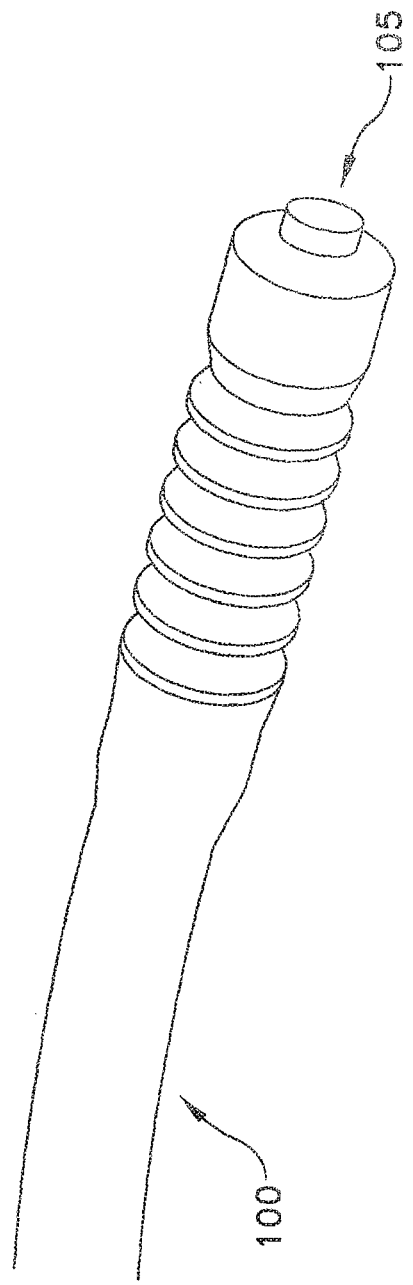
FIG. 22 is a schematic view showing the distal end of the guide catheter.
Figure 23:
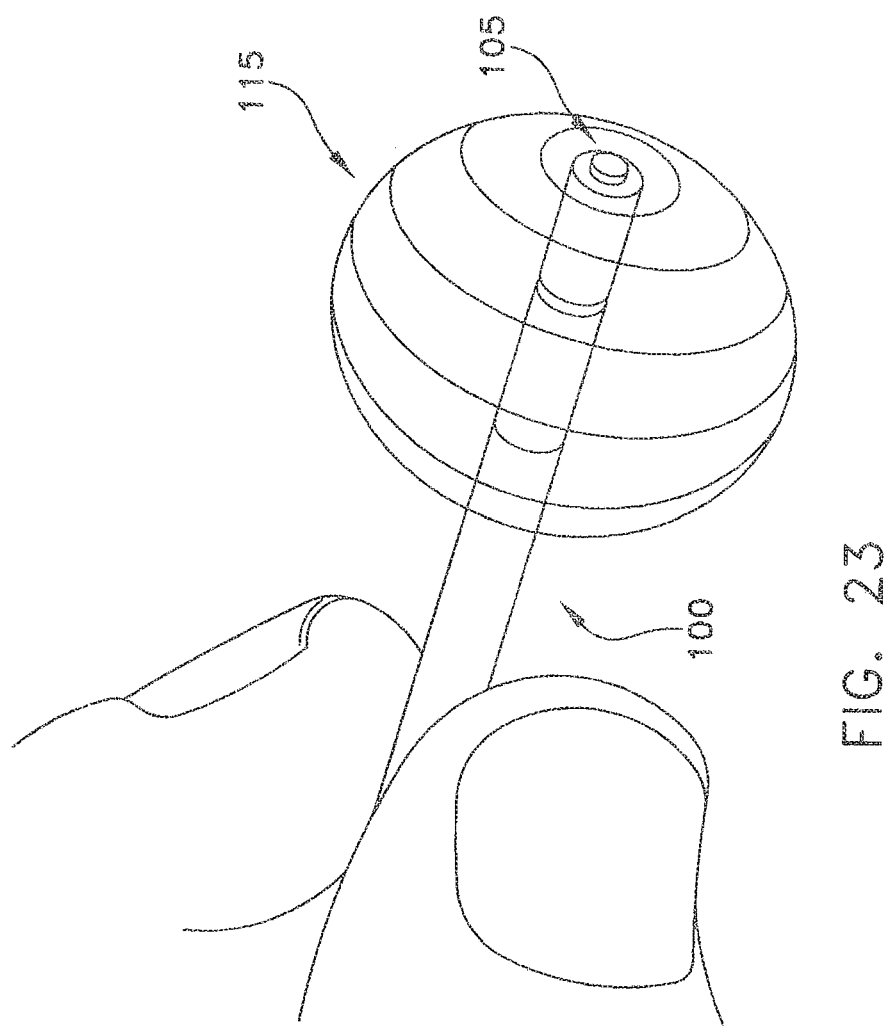
FIG. 23 is a schematic view showing the guide catheter's balloon in an expanded condition.

In one preferred form of use, guide catheter 100 is passed endoluminally across the atrial septum and into the left atrium. Guide catheter 100 (FIG. 22) has one or more magnets 105 at its tip. Magnets 105 are preferably so-called "rare earth" magnets composed of, for example, Neodymium-Iron-Boron, Cobalt-Samarium or other powerful fixed magnet elements. Just behind the magnets, preferably integral with and axi-symmetric to the body of the guide catheter, is inflatable balloon 115 (FIG. 23) which, when inflated, is spherical, conical, elliptical or of other configuration, and which preferably conforms roughly to the size and shape of the left atrial appendage 130. The entire guide catheter 100, inclusive of balloon 115 and magnets 105, is of a size consistent with passage through a commercially-available sheath (not shown), the likes of which may be readily passed across the atrial septum under fluoroscopic guidance using currently available tools and techniques.

In one preferred use of this system, the practitioner gains percutaneous access to the femoral vein using the Seldinger or other standard technique, and the aforementioned sheath (not shown) is introduced under fluoroscopic guidance across the atrial septum. The magnetic tip 105 of the guide catheter is then advanced out of the aforementioned sheath and into the left atrial appendage, in the manner previously discussed.

Figure 24:
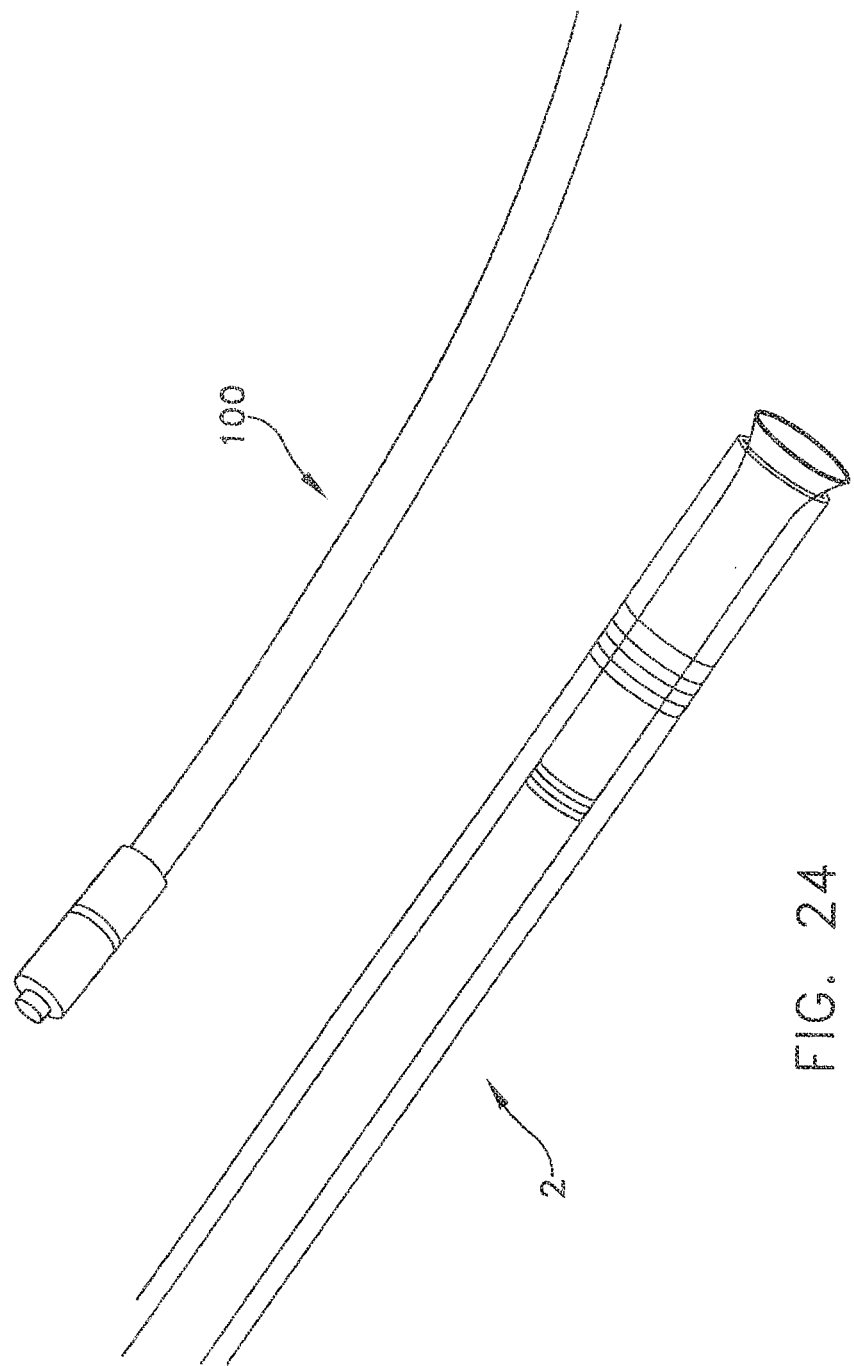
FIG. 24 is a schematic view showing the ligating catheter and the guide catheter.

The second instrument used with this iteration (i.e., the ligating catheter 2, as shown in FIG. 24) is introduced into the pericardial space, between the heart and the pericardium. Pericardial access may be obtained, for example, by either a small incision below the xiphoid process of the sternum, or by percutaneous access using needles or dedicated systems designed for such purposes. Under fluoroscopic guidance, a wire is introduced into the pericardial space, between the heart and the pericardial sack. Similarly, pericardial access can be obtained by way of a mini-thoracotomy or by a "Chamberlain"-type incision over the 2nd costal cartilage. Percutaneous access using dedicated systems designed for such purposes is generally preferred as it can be done under local anesthesia. An incision over the $2^{nd}$ costal cartilage, or a small incision below the xiphoid, is generally preferred to approaches that require violation of the left pleural space.

Figure 25:
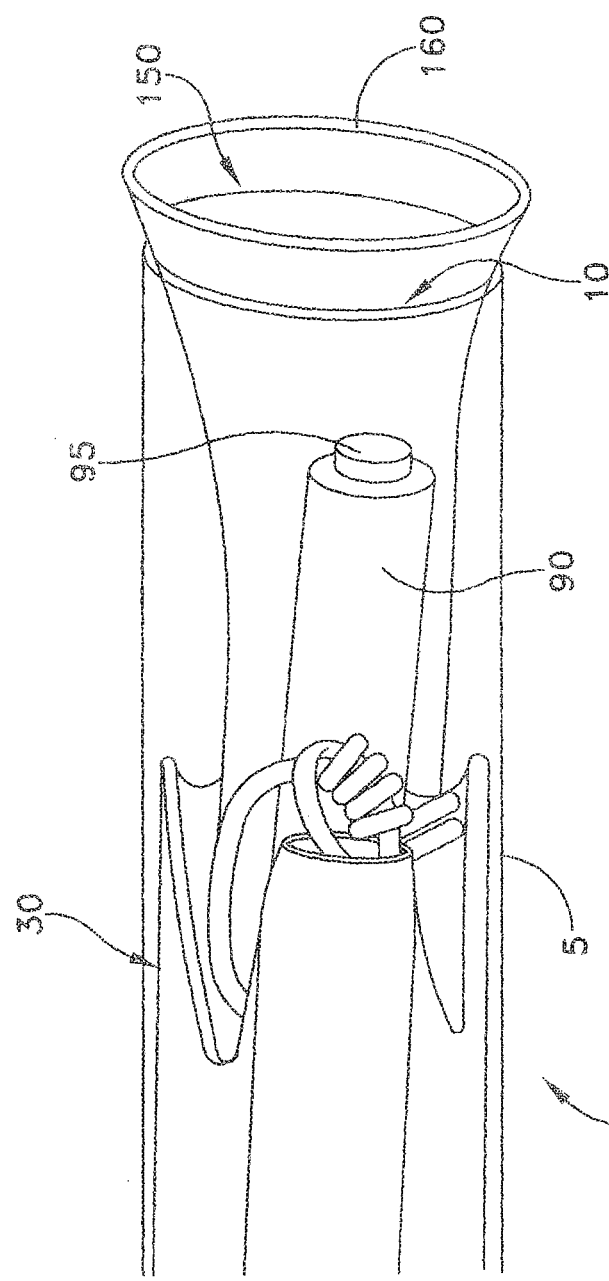
FIG. 25 is a schematic view showing the distal end of the ligating catheter.

Once pericardial access is obtained, the second instrument (i.e., the ligating catheter 2, as shown in FIG. 25) is introduced to the surgical site. In a preferred embodiment, the second instrument is preceded by a series of dilators and sheaths that are introduced over wires. The dilators are of a progressively increasing size culminating in the placement of a large thin-walled tube or cylinder 5, approximately 24 French or smaller, positioned such that its distal end is in the region of the left atrial appendage. This thin-walled tube 5 then acts as a delivery cannula for advancing the ligating subassembly 30 to the surgical site. In one iteration, the distal end 10 of the thin-walled tube 5 is deflectable by an asymmetric element that can be placed under tension. Alternatively, the thin-walled tube may have a permanent angulation or curve at its tip.

Once the thin-walled tube 5 is in position, the intrapericardial tool (i.e., the ligating subassembly 30) is advanced down the thin-walled tube 5. In a preferred embodiment, the ligating catheter 2 comprises a central intrapericardial catheter or alignment element 90 at the end of which is one or more rare-earth magnets 95, as described previously. These magnets 95 are poled to attract the ligating catheter 2 to the guide catheter 100 (previously placed in the left atrial appendage) in an end-to-end orientation. The ligating catheter 2 may be flexible or, in another embodiment, is stiff with a malleable, deflectable tip.

Coaxial to this alignment element 90, and constructed in such a manner that it can be advanced or withdrawn relative to either the alignment element 90 or the thin-walled tube 5, is a tube 150 that ends in a funnel-like or trumpet-bell flare 160. The internal diameter of this flared tube 150 is significantly larger than the external diameter of the intrapericardial magnet-tipped alignment element 90 (over which the flared tube 150 slides) so as to allow vacuum to be conveyed from the back of the flared tube 150 to the distal flare 160. This flared end 160 acts as a suction cup to grasp the tip of the left atrial appendage 130 from outside the heart.

Figure 26:
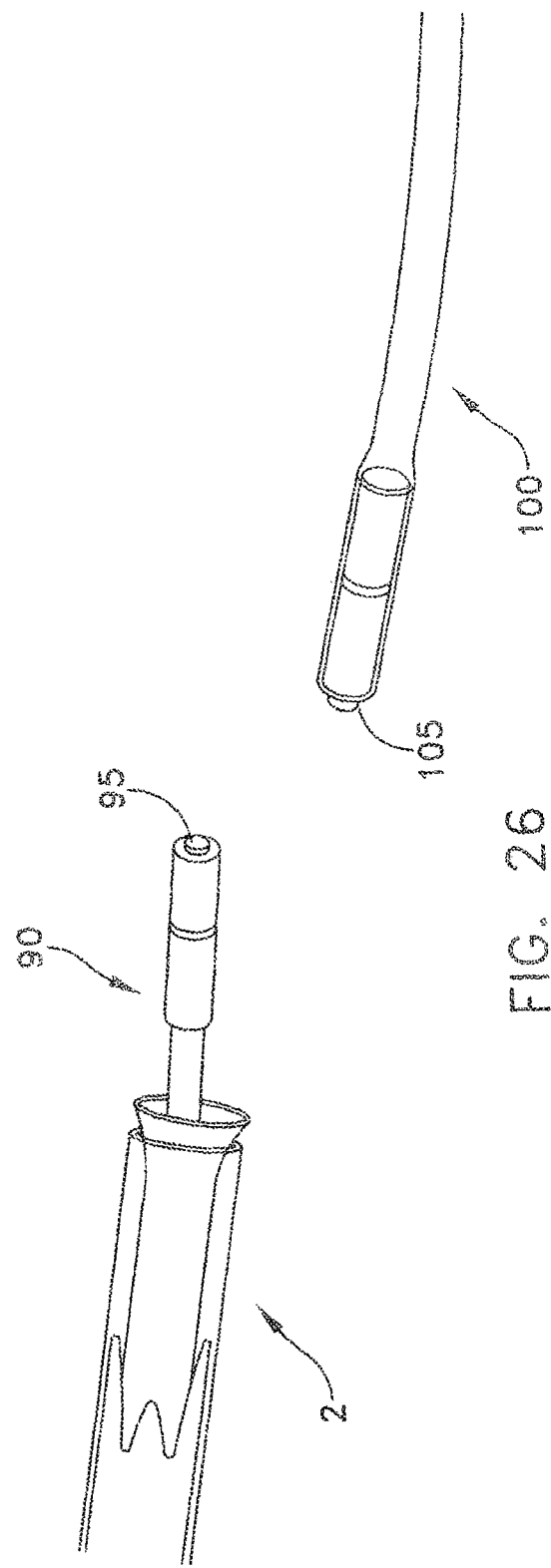
FIGS. 26 and 27 are schematic views showing the distal ends of the ligating catheter and the guide catheter orienting an end-to-end fashion through the use of magnets.
Figure 27:
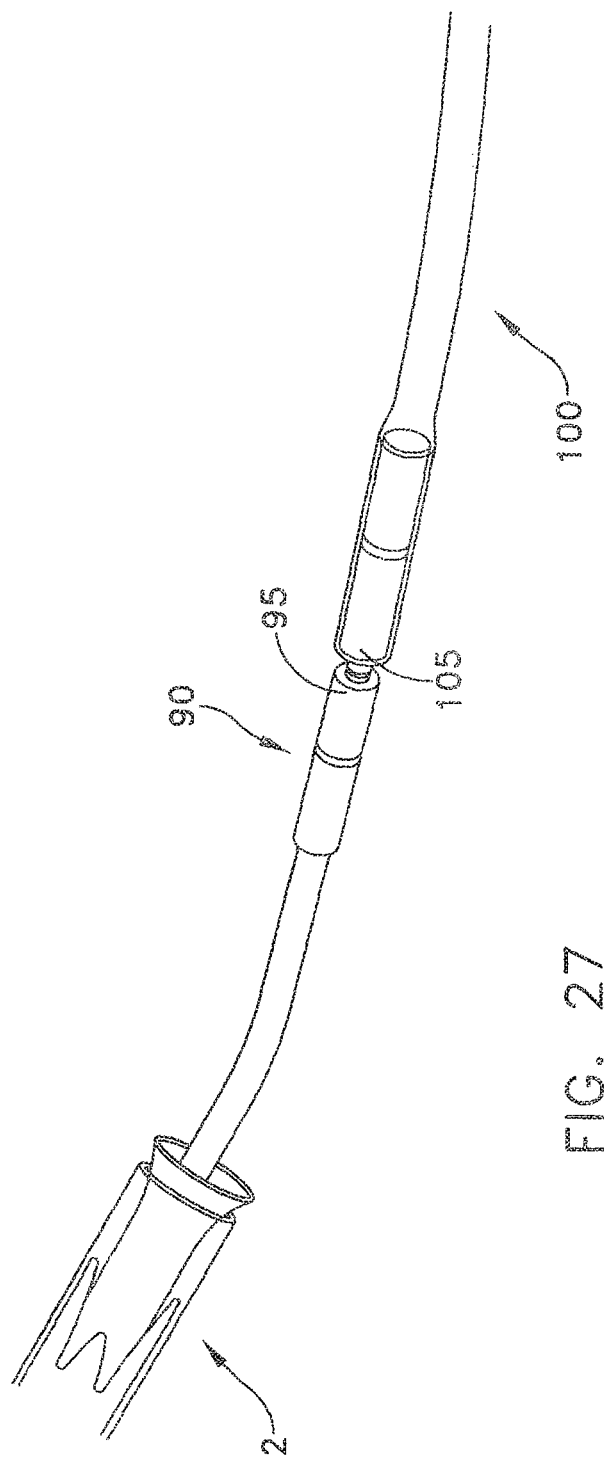
Figure 28:
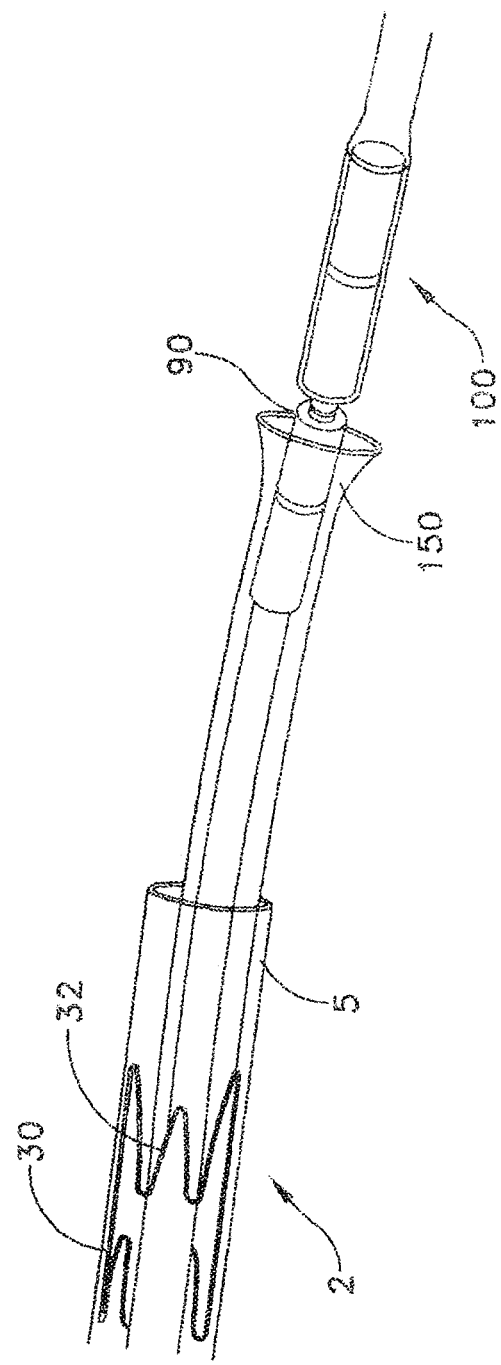
FIG. 28 is a schematic view showing a flared suction tube extending out of the ligating catheter's outer tube.

In a preferred embodiment, the ligating catheter's alignment element 90 is advanced (FIG. 26) under fluoroscopic guidance until it engages, and couples with, the guide catheter 100 (FIG. 27), which was previously placed across the atrial septum and into the inside of the left atrial appendage. Once such alignment has been achieved, and magnetic coupling confirmed by fluoroscopy, the flared tube 150 is advanced (FIG. 28) until it comes into contact with the outside of the left atrial appendage. Suction is then applied to the back of the flared tube 150, such that the left atrial appendage is fixed to the tip of the flared tube by vacuum.

Figure 29:
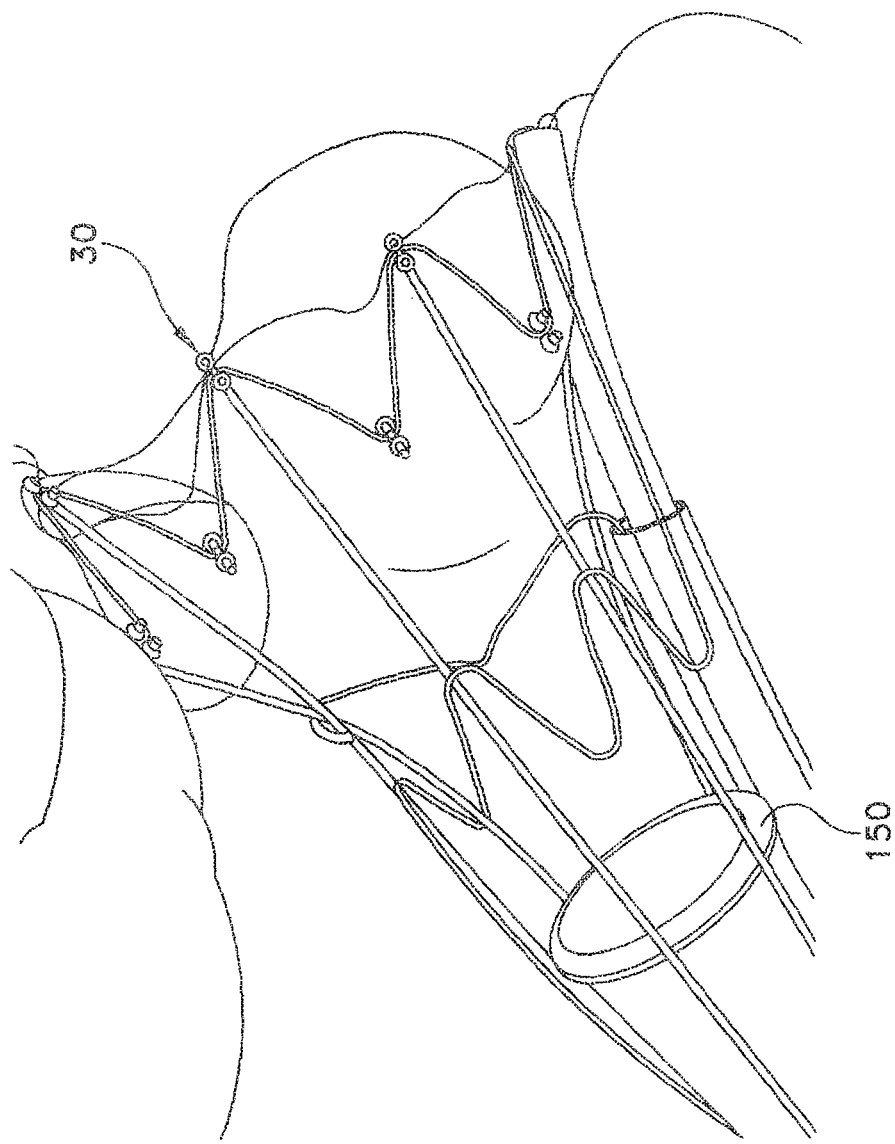
FIG. 29 is a schematic view showing details of the ligating subassembly.

Over the outside of this flared tube 150, but inside the lumen of the 24 French thin-walled tube 5, is a Nitinol stent-like structure or ligation subassembly 30 that can be advanced down the thin-walled tube 5 toward the tissue by way of a stiff catheter or other structure (i.e., the advancement/retraction control element 20) attached to its back end. This Nitinol structure 30 is designed to expand (once released from the constraints of the thin-walled outer tube 5) into a bell shaped crown (FIG. 29), the tips of which attach (circumferentially) the loop of a snare (i.e., the ligating element 32). In a preferred embodiment, the ligating element or snare 32 is composed of polypropylene or PTFE suture. The snare loop 32 is secured to the tips of the crown 30 in a reversible, easy-to-release fashion.

Once the left atrial appendage is secured with suction, the Nitinol structure 30, and its attached snare 32, is advanced over the flared tube 150 toward the left atrial appendage. The flared tube 150 extends 2 or 3 centimeters beyond the end of the thin-walled outer tube 5. As such, the Nitinol structure 30 begins to expand into a bell-shape which facilitates its advancement over the flared suction catheter 150, and over the left atrial appendage.

Figure 30:
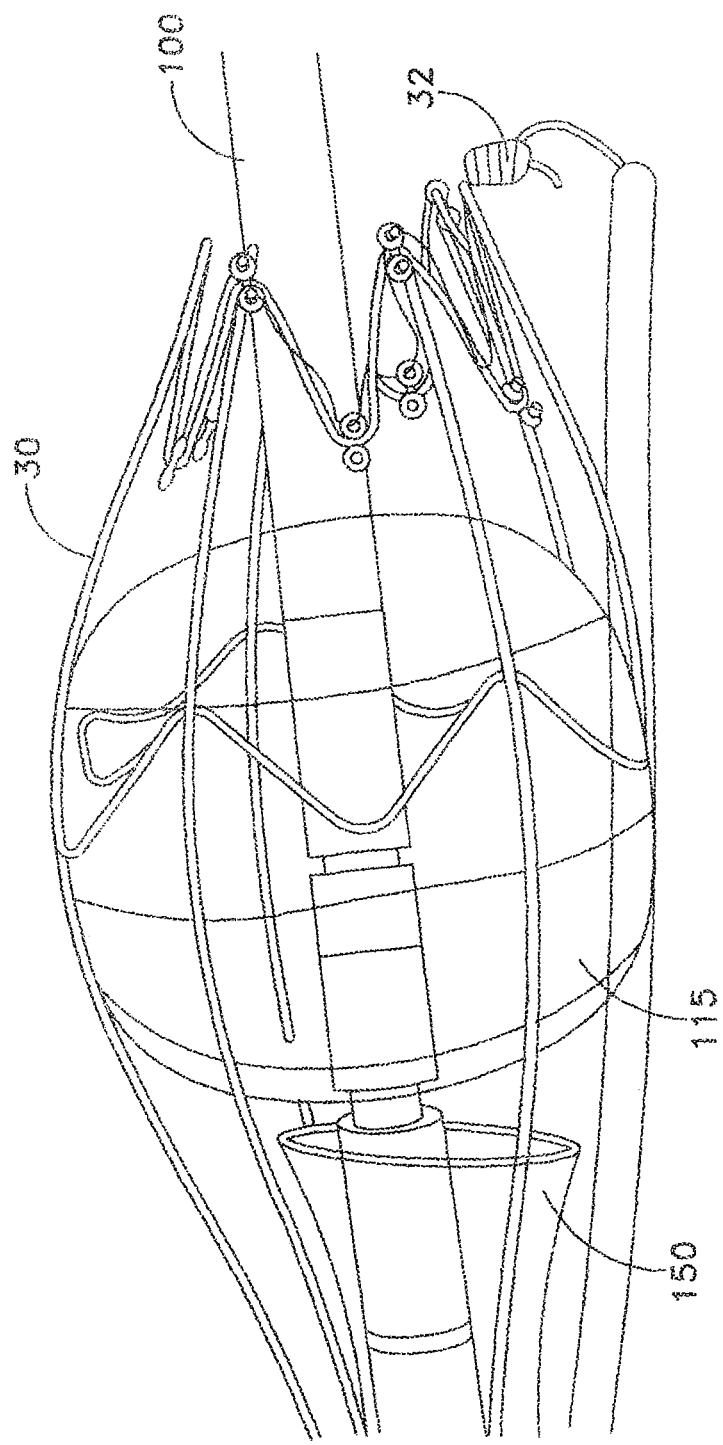
FIG. 30 is a schematic view showing the ligating subassembly extending over the guide catheter's inflated balloon.
Figure 31:
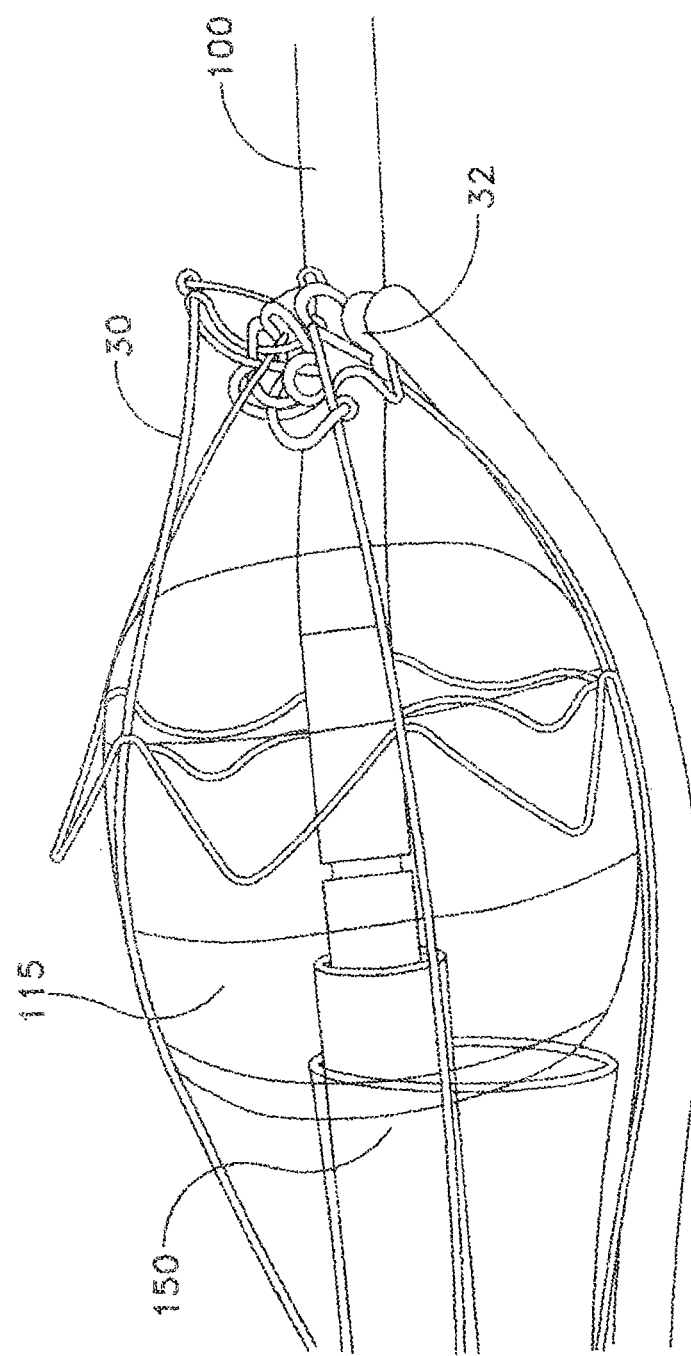
FIG. 31 is a schematic view showing the ligature being drawn taut on the outboard side of the guide catheter's balloon.

Once the Nitinol structure 30 has been advanced to the point where it is near the base of the left atrial appendage, the balloon 115 on the guide catheter 100 inside the appendage is inflated, preferably with a contrast material. The Nitinol structure is advanced under fluoroscopic guidance so that the tips of its bell-shaped crown 30 (and the suture snare 32) are beyond the inter-atrial balloon (FIG. 30). The snare 32 is then tightened by pulling on a strand of the suture that runs down the lumen of the stiff catheter 20 which is used to advance the Nitinol structure 30 (FIG. 31). With the suture snared, the guide catheter's balloon is deflated and the trans-septal left atrial catheter 100 is removed. The suture snare 32 is then preferably tightened again to account for the space previously occupied by the inter-atrial catheter 100. The Nitinol structure 30 releases away from the suture snare 32 when the snare is tightened. The ligating catheter 2 is then removed and the suture is cut at the skin.

Additional Constructions

Figure 32:
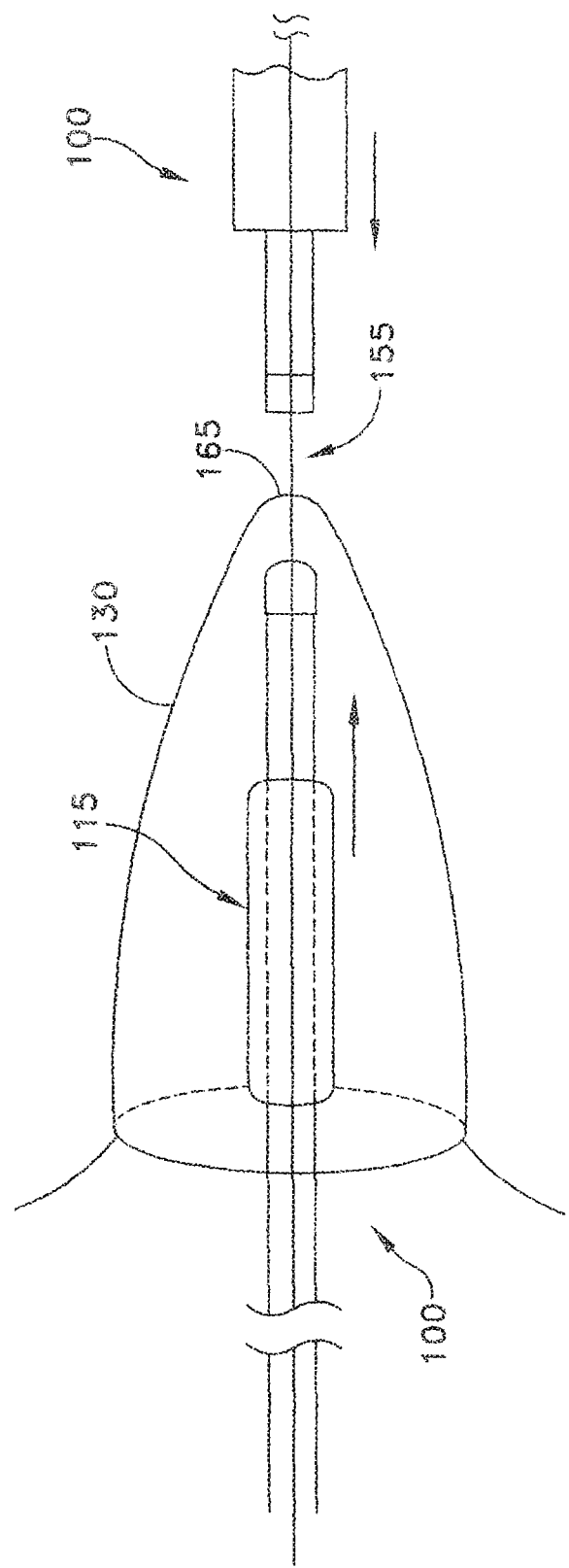
FIG. 32 is a schematic view showing a single wire track passing from the interior of the left atrial appendage out through the pericardium, whereby a guide catheter and/or a ligating catheter may be advanced to the surgical site.

In a preferred form of the present invention, and looking now at FIG. 32, a wire 155 is passed through the left atrial appendage 130, through the wall of the left atrial appendage 130 and advanced through the pericardial space, whereby tip 165 of the left atrial appendage is perforated. Wire 155 can then be grasped by a catheter or snare in the pericardial space and pulled all the way through the pericardium and then out of the body, thereby creating a single wire track on which guide catheter 100, ligating catheter 2, and/or other devices can be passed along from either end of wire 155. With this construction, alignment element 90 on ligating catheter 2, and/or alignment element 102 on guide catheter 100 may be omitted if desired. Furthermore, with this embodiment of the invention, guide catheter 100 may be omitted altogether if desired.

Additionally, if desired one or more of the magnets 95 and/or 105 may comprise an electromagnet. Such a construction permits the magnetic field to be selectively turned on and off, thus facilitating separation of the devices at the end of the procedure.

Furthermore, in the foregoing description, struts 45 are described as being preferably expanded by connecting them to one another with springs 50, whereby to render the struts self-expandable when they are advanced out of the distal end of cylinder 5. Alternatively, struts 45 may be expanded by other means, e.g., an expansion mechanism mounted to struts 45, or by making struts 45 out of a spring material (e.g., a superelastic material such as Nitinol), etc.

Addition Aspects of the Present Invention

In one preferred form of the invention, the novel apparatus and method uniquely combine two or more of the following components:
  (1) an elongated element such as a cylinder;
  (2) an expandable element to help place the ligature over the tissue to be ligated;
  (3) the ligature;
  (4) an alignment mechanism; and
  (5) an expandable element that helps guide the ligature into its proper position as the ligature is deployed.

In one aspect of the invention, an alignment system is provided for positioning a ligature delivery apparatus at a desired location around a tissue structure such as the left atrial appendage.

In another aspect of the invention, a tissue expander is provided for positioning a ligature at a desired location around a tissue structure such as the left atrial appendage.

And in another aspect of the invention, a radially-adjustable ligature delivery apparatus is provided for positioning a ligature at a desired location around a tissue structure such as the left atrial appendage. This delivery apparatus may be expandable.

In still another aspect of the invention, there is provided a ligature system which includes an alignment system, a tissue expander, and a radially-adjustable ligature delivery apparatus, and which is configured to position a ligature around a tissue structure such as a left atrial appendage.

And in still another aspect of the invention, there is provided a ligature system configured to position a ligature around a tissue structure such as the left atrial appendage without opening the chest.

And in still another aspect of the invention, there is provided a ligature system configured to position a ligature around a tissue structure such as the left atrial appendage without opening the chest, using at least two catheters entering the body from remote locations such as a vein, artery and/or through the skin.

In another aspect of the invention, there is provided a novel system comprising a guide member configured for placement within the left atrial appendage of a patient and adapted to provide a reference for positioning a ligature at a desired location around the left atrial appendage.

In yet another aspect of the invention, there is provided a ligature delivery apparatus having an alignment component configured for positioning a ligature at a desired location in response to the reference of the aforementioned guide member disposed within the left atrial appendage.

In still another aspect of the invention, there is provided a tissue expander configured for placement within the left atrial appendage and adapted to define a desired location for positioning a ligature.

In still another aspect of the invention, there is provided a reference catheter having both a guide member and a tissue expander for placement within the left atrial appendage.

In still another aspect of the invention, there is provided a radically-adjustable ligature delivery apparatus configured for placing a ligature at a desired location around the left atrial appendage of a patient.

In still another aspect of the invention, there is provided a delivery catheter having both an alignment component corresponding to the aforementioned guide member within the left atrial appendage of a patient and an adjustable ligature delivery apparatus for placing the ligature therearound.

In still another aspect of the invention, there is provided a delivery catheter having both an alignment component corresponding to the aforementioned guide member within the left atrial appendage of a patient and an adjustable ligature delivery apparatus for placing the ligature therearound, whereby the delivery apparatus contains an expandable element.

In still another aspect of the invention, there is provided a ligature system including both a reference catheter and an alignment catheter configured to correspond with one another so as to place a ligature at a desired location around the left atrial appendage of a patient.

In still another aspect of the invention, there is provided a ligature system including both a reference catheter and an alignment catheter configured to correspond with one another so as to place a ligature at a desired location around the left atrial appendage of a patient, in which either the reference catheter or the alignment catheter, or both, include an expandable element.

In another aspect of the invention, a device incorporating one or more of the above-identified components is placed in proximity to the tissue which is to be ligated. This can be done in many ways such as under direct visualization or under fluoroscopic, ultrasound, radiographic, CT, MRI, etc., guidance. Additionally, it can be further aligned by using such devices as alignment strands, magnets, etc.

And in another aspect of the invention, the apparatus and method may be used to ligate the left atrial appendage as follows. Access to the pericardial space is acquired using standard techniques such as the Seldinger over-the-wire technique. For example, such device, which preferably comprises an elongated device such as a cylinder containing an expandable element, a ligature, and an alignment mechanism, is placed into the pericardium over a guidewire. For example, the elongated device can be a large catheter in which there is an expandable element, a ligature, and an alignment mechanism.

And in another aspect of the invention, a guide catheter is placed into the left atrium using standard techniques, such as transseptally, through the veins or retrograde across the mitral valve, etc. The guide catheter in the left atrium is then placed into the left atrial appendage under fluoroscopic guidance. At this point, the guide catheter is in the left atrial appendage and the ligating mechanism is disposed in connection with a deployment catheter in the pericardial space. The guide catheter in the left atrium and the deployment catheter in the pericardial space are then aligned with one another. This can be done using a variety of techniques. For example, one or both of the devices can be magnetized, thus allowing them to be aligned relative to one another using magnetic force. Alternatively, the guide catheter and deployment catheter can be "steered" into proximity using visual or ultrasonic guidance. Or the guide catheter in the left atrium can penetrate the left atrial appendage and be "snared" by the deployment catheter in the pericardium. At this point, the device in the pericardium is advanced into proximity with the left atrial appendage. A ligating apparatus is then deployed from the deployment catheter and advanced over the left atrial appendage. Preferably, the guide catheter inside the left atrium includes an expandable element such as a balloon. This expandable element is then expanded inside the left atrial appendage. In so doing, this expansion helps prevent the ligature from slipping or migrating off of the left atrial appendage as the ligature is tightened around the left atrial appendage. The ligature is then tightened around the left atrial appendage. The expandable element inside the left atrium is then contracted. The guide catheter inside the left atrial appendage is then backed out of the left atrial appendage. The procedure can be repeated as necessary. The guide catheter and deployment catheter are then removed from the body cavity.

Alternatively, the guide catheter inside the left atrial appendage may be removed after the ligature has been mostly placed, but before the final tightening of the ligature. This will allow the base of the left atrial appendage to be completely occluded after the guide catheter is withdrawn from the left atrial appendage.

The following text further illustrates a preferred manner for ligating the left atrial appendage. A trans-septal left atrial guide catheter that has (integral to its construction) a rare-earth magnet, or other alignment means, and an inflatable balloon, is of great utility in effectively occluding the left atrial appendage with a snare or ligature. The left atrial appendage is typically roughly conical in shape, with a slight neck or narrowing in the plane of the orifice where it joins the left atrium proper. To effectively exclude the left atrial appendage from the outside with a ligature or snare, the snare must be tightened precisely in this plane. Ideally, with the ligature tightened, the resultant left atrial geometry should be essentially spherical, with only a slight dimple visible from the endocardial or luminal aspect at the site of the obliterated orifice. If the snare is tightened above the plane of the orifice (toward the left atrial appendage tip), incomplete exclusion of the left atrial appendage may result in a persistent diverticulum of left atrial appendage, which may provide a site of stasis and thrombus formation in the fibrillating atrium. Conversely, if the snare is tightened below the plane of the orifice, there is a risk of injury to the circumflex coronary artery, which runs in the atrio-ventricular grove.

Snaring the left atrial appendage precisely and accurately in the optimal plane presents several technical challenges. In some individuals, the geometry of the left atrium and left atrial appendage may be such that the neck or narrowing between them is poorly defined, especially from the epicardial or outer aspect. Furthermore, because the left atrial appendage wall is thin and flexible, and the wall tension low (left atrial pressure is generally low, e.g., <20 mm Hg), the external geometry of the left atrial appendage-left atrial junction may be of little help in constraining the snare to the correct plane during tightening. This challenge is compounded by the fact that the anatomy is moving vigorously, even in the fibrillating atrium, due to translational motion from ventricular systole. A trans-septal left atrial guide catheter equipped with a magnetic tip and a large inflatable balloon such as described above enables snaring the left atrial appendage in the proper plane. More particularly, it is believed that identifying and capturing the tip of the left atrial appendage using just an intra-pericardial instrument under fluoroscopic or echocardiographic guidance may prove prohibitively challenging. At the same time, passing a catheter across the atrial septum into the left atrium, and subsequently positioning it in the apex of the left atrial appendage, is readily accomplished by those skilled in the art with catheters that are commercially available. Thus, positioning a guide catheter with a rare-earth magnet (or other alignment mechanism) at the tip thereof in the left atrial appendage is readily achievable and thereby allows fluoroscopic guidance as to the position of the left atrial appendage apex, as well as enabling precise capturing of the apex with an intra-pericardial tool.

A balloon near the tip of the trans-septal left atrial guide catheter greatly facilitates positioning and tightening of the snare or ligature in the proper plane of the orifice between the left atrial appendage and left atrium. Preferably, the balloon is designed to inflate to approximately the size of the left atrial appendage. As the balloon is inflated, it is confined to the left atrial appendage by the neck or narrowing at the orifice between left atrial appendage and left atrium. This may be readily confirmed by echocardiographic examination, or fluoroscopy, especially if the balloon is inflated with a contrast agent. Separate ports in the guide catheter allow the contrast agent to be injected into the left atrial appendage and/or the left atrium proper to provide further confirmation of correct position of the inflated balloon.

The inflated balloon accentuates external geometric features at the left atrial appendage-left atrial junction. When the spherical balloon is inflated, the flexible left atrial appendage is distended and its shape changed (e.g., to spherical) to facilitate ligation. The junction between the left atrial appendage and left atrium becomes better defined, like a waist of a snowman. This constrains the snare or ligature to the proper plane during tightening. The balloon, and consequently the left atrial appendage, is inflated to a pressure significantly higher than that of the left atrium proper. As such, there is a significant differential in wall tension between the left atrial appendage and the left atrium. As the balloon is spherical, an attempt at snaring above the plane will result in the snare slipping off of the tense spherical surface toward the low tension, flexible neck. Radio-opaque contrast agent in the balloon, the ability to selectively inject contrast in the left atrial appendage and/or left atrium proper, and a radio-opaque snare or ligature greatly facilitate performing these procedures under fluoroscopic guidance. Once the left atrial appendage-left atrial junction is snared, the balloon is deflated and removed and the snare tightened completely.

In general, it should be appreciated that, among other things, the invention comprises the alignment of two devices, one within and one outside of a lumen, cardiac chamber, etc. Thus, the present invention could be used in the stomach to help with an endoscopic fundiplication.

The foregoing description is intended to illustrate preferred embodiments of the present invention. However, numerous changes may be made to the preferred embodiments without departing from the scope of the present invention. Thus, one or more of the steps of the method, and/or one or more of the components of the apparatus, may be modified or omitted. Also, the present apparatus and method may be used to ligate any tissue or like structure in the body.

What is claimed is:

1. A method for positioning a device near a patient's heart comprising:
    advancing a first alignment element transeptally into a left atrial appendage, wherein the first alignment element is coupled to a guide device comprising an expandable element;
    expanding the expandable element relative to the first alignment element;
    advancing a second alignment element into a pericardial space from outside a patient's heart; and
    aligning the first and second alignment elements to assist in positioning the device.

2. The method of claim 1, wherein aligning the first and second alignment elements assists in positioning the device in the pericardial space.

3. The method of claim 2, wherein aligning the first and second alignment elements assists in positioning the device at a neck of the left atrial appendage.

4. The method of claim 1, wherein the device comprises a ligating element and the method further comprises advancing the ligating element to the left atrial appendage.

5. The method of claim 4 further comprising ligating the left atrial appendage with the ligating element.

6. The method of claim 4, wherein advancing the ligating element to the left atrial appendage comprises advancing the ligating element relative to the second alignment element.

7. The method of claim 1, wherein the alignment elements are aligned end-to-end.

8. The method of claim 1, wherein each of the first and second alignment elements comprises a magnet.

9. The method of claim 1, wherein the expandable element is an inflatable balloon.

10. The method of claim 1 further comprising expanding the expandable element within the left atrial appendage.

11. The method of claim 10 further comprising ligating the left atrial appendage with a ligating element, wherein the expanded expandable element is used to assist in positioning the ligating element around a neck of the left atrial appendage.

12. The method of claim 1, wherein the first alignment element comprises a magnet and the expandable element is positioned near a distal end of the guide device and proximal to the magnet.

13. The method of claim 1, wherein the first alignment element is visualized as it is advanced into the left atrial appendage using fluoroscopy or ultrasound.

14. The method of claim 1, wherein the pericardial space is accessed by making an incision below the xiphoid process.

15. The method of claim 1, wherein the pericardial space is accessed by using a series of dilators.

* * * * *